United States Patent
Kuennen et al.

(10) Patent No.: US 7,252,763 B2
(45) Date of Patent: Aug. 7, 2007

(54) POINT-OF-USE WATER TREATMENT SYSTEM

(75) Inventors: Roy W. Kuennen, Caledonia, MI (US); Eric K. Bartkus, Ada, MI (US); David W. Baarman, Fennville, MI (US); Kenneth E. Conrad, Ada, MI (US); Terry L. Lautzenheiser, Numica, MI (US); Greg Snyder, Novato, CA (US); Scott A. Mollema, Grand Rapids, MI (US)

(73) Assignee: Access Business Group Interational LLC, Ada, MI (US)

( * ) Notice: Subject to any disclaimer, the term of this patent is extended or adjusted under 35 U.S.C. 154(b) by 424 days.

(21) Appl. No.: 10/767,035

(22) Filed: Jan. 29, 2004

(65) Prior Publication Data

US 2004/0182761 A1    Sep. 23, 2004

Related U.S. Application Data

(62) Division of application No. 10/207,528, filed on Jul. 29, 2002, now Pat. No. 6,793,817, which is a division of application No. 09/596,416, filed on Jun. 12, 2000, now Pat. No. 6,451,202.

(60) Provisional application No. 60/140,159, filed on Jun. 21, 1999, provisional application No. 60/140,090, filed on Jun. 21, 1999.

(51) Int. Cl.
*C02F 1/32* (2006.01)
(52) U.S. Cl. .................... 210/192; 422/186.3; 250/435
(58) Field of Classification Search .................. 422/24, 422/186.3; 210/748, 192; 250/436, 435
See application file for complete search history.

(56) References Cited

U.S. PATENT DOCUMENTS

| 723,836 A | 3/1903 | Cowing |
|---|---|---|
| 2,133,494 A | 10/1938 | Waters |
| 3,122,492 A | 2/1964 | Barnes et al. |
| 3,471,693 A | 10/1969 | Veloz |
| 3,745,410 A | 7/1973 | Fletcher et al. |
| 3,923,663 A | 12/1975 | Reid |
| 3,971,947 A | 7/1976 | Lambert et al. |
| 4,017,734 A | 4/1977 | Ross |
| 4,038,625 A | 7/1977 | Tompkins |
| 4,061,922 A | 12/1977 | Last |
| 4,201,916 A | 5/1980 | Ellner |
| 4,278,508 A | 7/1981 | White et al. |

(Continued)

FOREIGN PATENT DOCUMENTS

| DE | 29707052 | 11/1997 |
|---|---|---|
| EP | 0913628 | 5/1999 |
| GB | 0782546 | 9/1995 |
| JP | 60034784 A | 2/1985 |
| JP | 62027093 | 2/1987 |
| JP | 1067293 | 3/1989 |
| JP | 8039056 | 2/1996 |
| WO | WO 9633135 A1 * | 10/1996 |

*Primary Examiner*—Terry K. Cecil
(74) *Attorney, Agent, or Firm*—Warner Norcross & Judd LLP

(57) ABSTRACT

A lamp assembly for use in a water treatment system. The lamp assembly includes a bulb assembly, a reflector assembly and a conduit carring liquid, such as water, through the lamp assembly. The reflector assembly is configured to reflect and focus light emitted from the bulb assembly on the conduit, thereby enhancing the efficiency of the lamp assembly. The reflector assembly can include reflectors including one or more diminishing radii of curvature, which terminate and form a peak near a bulb of the bulb assembly and/or conduit.

13 Claims, 27 Drawing Sheets

U.S. PATENT DOCUMENTS

| | | |
|---|---|---|
| 4,303,514 A | 12/1981 | Theorell |
| 4,448,547 A | 5/1984 | Wickersheim |
| 4,642,512 A | 2/1987 | Matsuno et al. |
| 4,694,179 A | 9/1987 | Lew et al. |
| 4,710,638 A | 12/1987 | Wood |
| 4,780,197 A | 10/1988 | Schuman |
| 4,831,268 A | 5/1989 | Fisch et al. |
| 4,838,797 A | 6/1989 | Dodier |
| 4,885,471 A | 12/1989 | Telfair et al. |
| 4,948,980 A | 8/1990 | Wedekamp |
| 4,971,687 A | 11/1990 | Anderson |
| 5,069,782 A | 12/1991 | Moyher, Jr. et al. |
| 5,070,293 A | 12/1991 | Ishii et al. |
| 5,078,876 A | 1/1992 | Whittier et al. |
| 5,117,156 A | 5/1992 | Leyh et al. |
| 5,244,558 A | 9/1993 | Chiang |
| 5,247,178 A | 9/1993 | Ury et al. |
| 5,266,215 A | 11/1993 | Engelhard |
| 5,289,085 A | 2/1994 | Godyak et al. |
| 5,300,860 A | 4/1994 | Godyak et al. |
| 5,330,661 A | 7/1994 | Okuda et al. |
| 5,341,083 A | 8/1994 | Klontz et al. |
| 5,379,021 A | 1/1995 | Ito et al. |
| 5,381,073 A | 1/1995 | Godyak et al. |
| 5,477,430 A | 12/1995 | LaRose |
| 5,536,395 A | 7/1996 | Kuennen et al. |
| 5,540,848 A | 7/1996 | Engelhard |
| 5,586,879 A | 12/1996 | Szpak |
| 5,591,978 A | 1/1997 | Kovalsky et al. |
| 5,594,304 A | 1/1997 | Graber |
| 5,597,482 A | 1/1997 | Melyon |
| 5,612,001 A | 3/1997 | Matschke |
| 5,632,890 A | 5/1997 | Sugimoto |
| 5,635,133 A * | 6/1997 | Glazman ............... 422/24 |
| 5,695,168 A | 12/1997 | Williams |
| 5,698,091 A | 12/1997 | Kuennen et al. |
| 5,843,309 A | 12/1998 | Mancil |
| 5,858,227 A | 1/1999 | Stone et al. |
| 5,864,209 A | 1/1999 | Clark |
| 5,896,483 A | 4/1999 | Wojcik et al. |
| 5,900,178 A | 5/1999 | Johnsen |
| 5,914,037 A | 6/1999 | Yen |
| 5,935,431 A | 8/1999 | Korin |
| 5,973,455 A | 10/1999 | Mirskiy et al. |
| 6,004,458 A | 12/1999 | Davidson |
| 6,022,511 A * | 2/2000 | Matschke ............... 422/121 |
| 6,027,644 A | 2/2000 | Magnusson et al. |
| 6,035,266 A | 3/2000 | Williams et al. |
| 6,037,598 A | 3/2000 | Cicha |
| 6,042,720 A | 3/2000 | Reber et al. |
| 6,099,799 A | 8/2000 | Anderson |
| 6,245,229 B1 | 6/2001 | Kool et al. |
| 6,404,111 B1 | 6/2002 | Kunkel |

\* cited by examiner

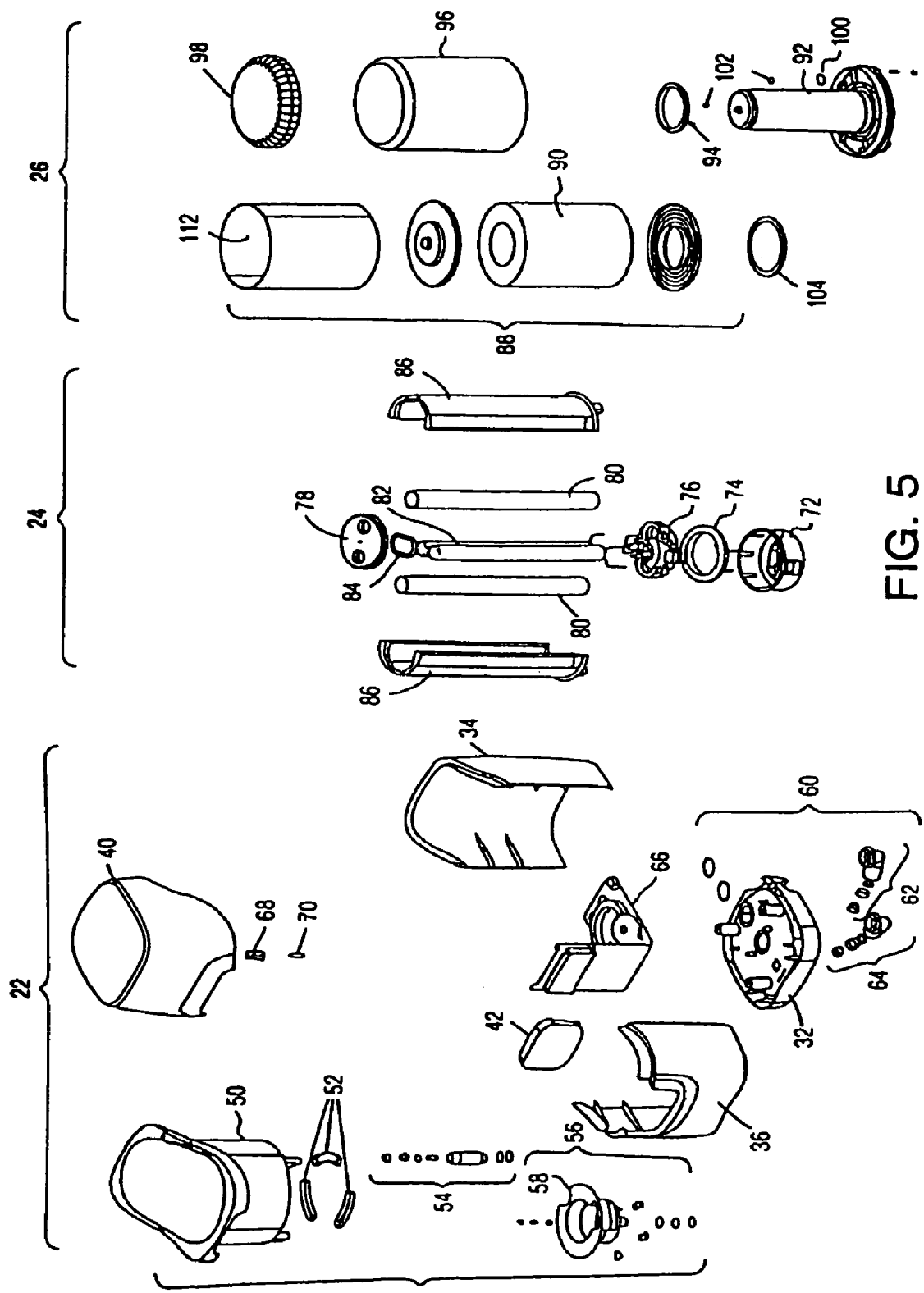

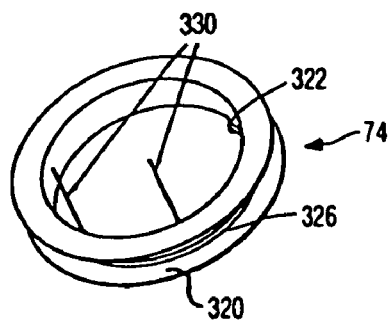
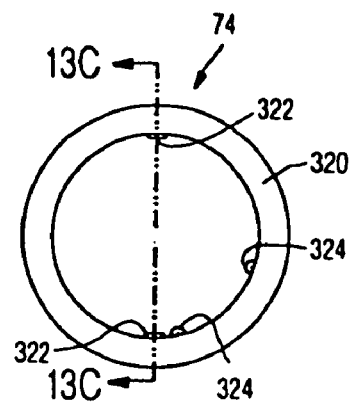
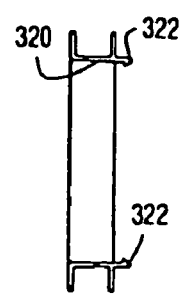
FIG. 13A  FIG. 13B  FIG. 13C
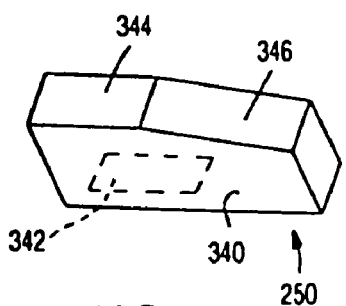
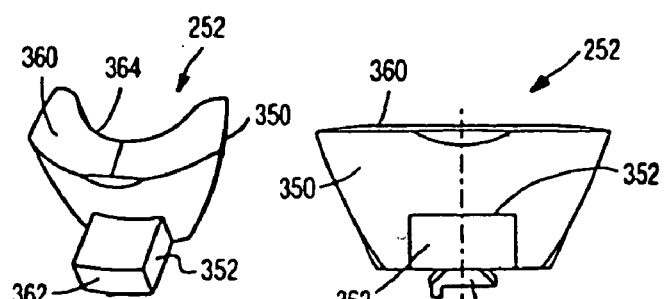
FIG. 14  FIG. 15A  FIG. 15B
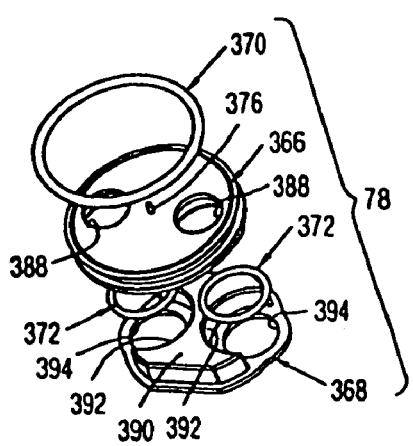
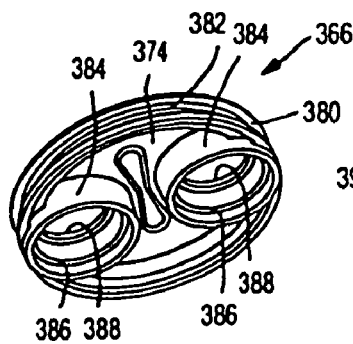
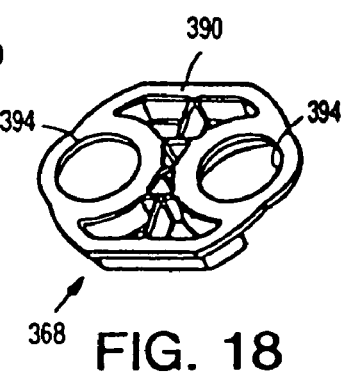
FIG. 16  FIG. 17  FIG. 18

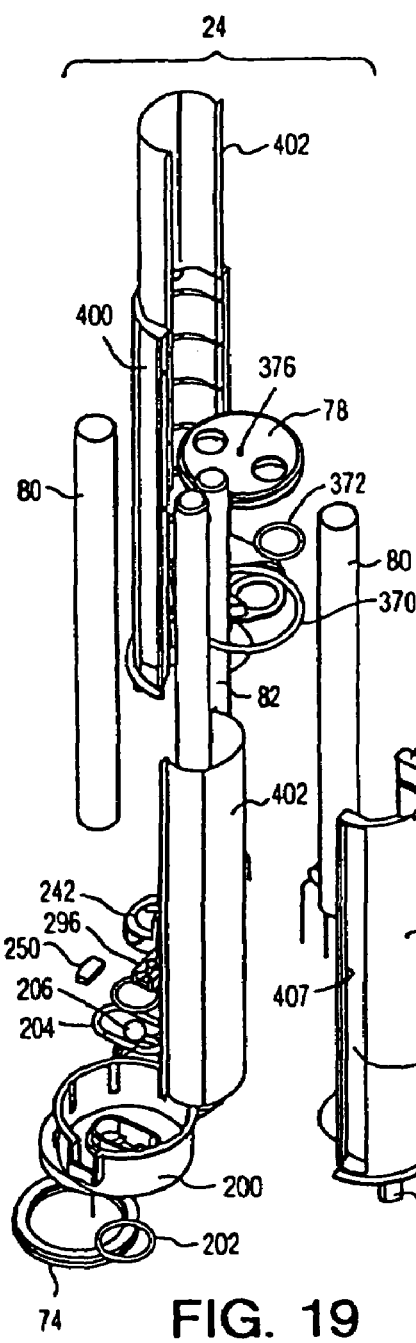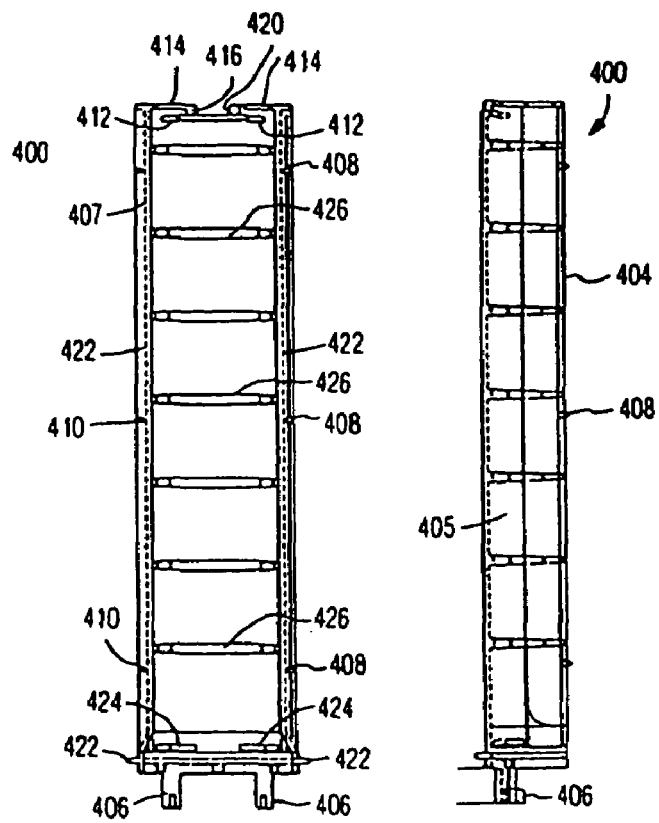
FIG. 19   FIG. 20A   FIG. 20B

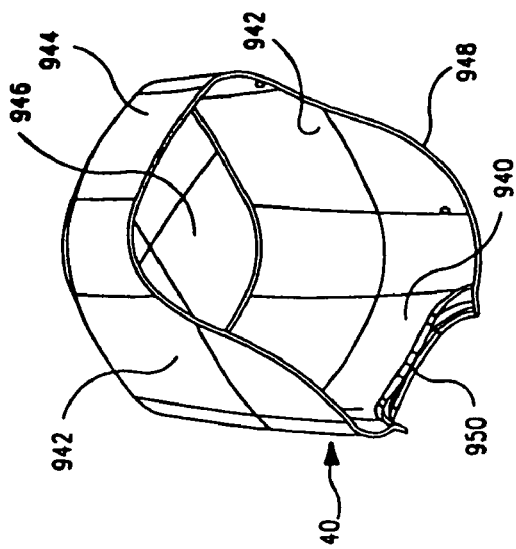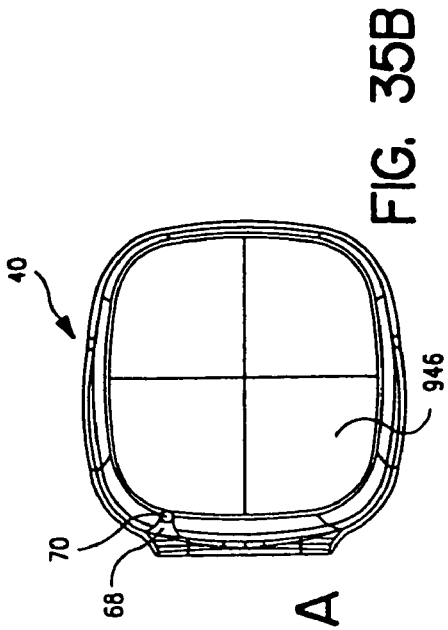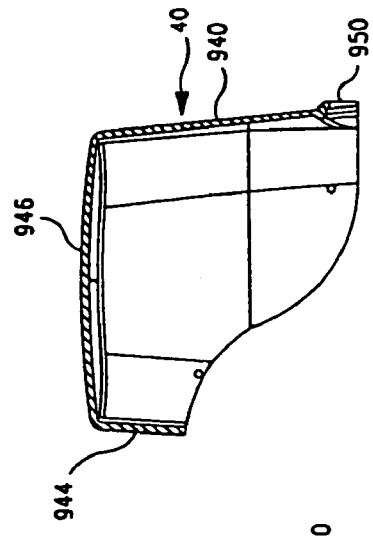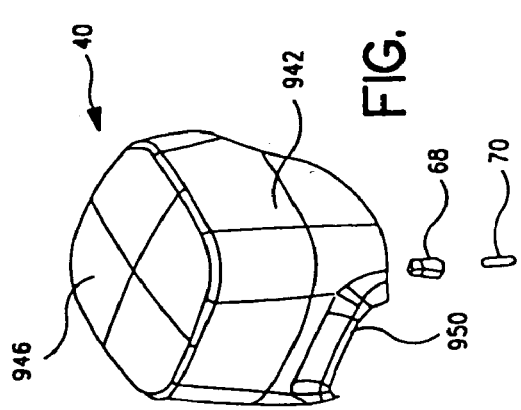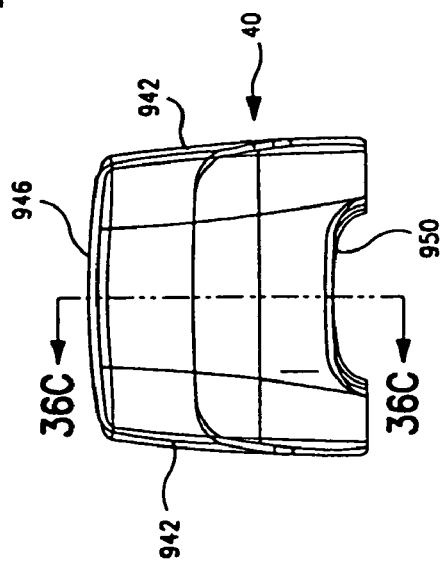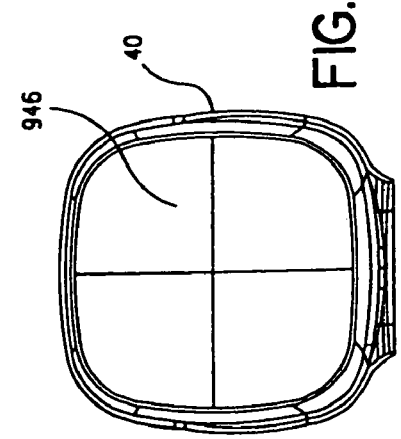

POINT-OF-USE WATER TREATMENT SYSTEM

This is a divisional of application Ser. No. 10/207,528, filed Jul. 29, 2002 now U.S Pat No. 6,793,817 which is a divisional of application Ser. No. 09/596,416, filed Jun. 12, 2000 (now U.S. Pat. No. 6,451,202), which claims priority under 35 U.S.C. §119(e) to provisional application Ser. No. 60/140,090, filed Jun. 21, 1999, titled "Point-of-Use Water Treatment System," and provisional application Ser. No. 60/140,159, filed Jun. 21, 1999, titled "Water Treatment System With An Inductively Coupled Ballast," the entirety of each of which is incorporated herein by reference. Also, incorporated by reference is the disclosure contained in U.S. patent application Ser. No. 09/592,194, filed Jun. 12, 2000, titled "Fluid Treatment System."

TECHNICAL FIELD

The present invention relates to point-of-use water treatment system (WTS) units used in homes and offices to filter and treat contaminants in water.

BACKGROUND OF THE INVENTION

The present invention minimizes or overcomes several problems associated with previous point-of-use home or office water treatment system (WTS) units. A first problem is that conventional WTS units, utilizing lamp assemblies with UV bulb assemblies therein, are energy inefficient. When a conventional lamp assembly is turned on, it takes a significant amount of start-up time before gases within a UV bulb assembly are sufficiently excited to output light of an intensity level required to insure adequate destruction of microorganisms within the WTS unit. Water which is discharged from the WTS unit before a UV bulb assembly is sufficiently excited and microorganisms properly irradiated may carry an unacceptably high level of live microorganisms. Consequently, conventional lamp assemblies are left continuously running which uses a significant amount of energy. Also, with the lamp assembly left running continuously, such as overnight, water residing within a WTS unit can become uncomfortably warm. Finally, the life expectancy of a lamp assembly which is kept running continuously is significantly reduced relative to a lamp assembly which is only activated when water is to be treated.

A second problem is with the design of reflector assemblies within WTS units. In an attempt to increase lamp efficiency, reflector assemblies may be placed about UV bulb assemblies and water carrying conduits in which the microorganisms are irradiated. Light emitted from a UV bulb assembly which misses striking water carrying conduits is reflected back from the reflectors walls and has a chance to again impinge upon the water carrying conduits. These reflector assemblies may be circular in cross-section. Unfortunately, a lot of the UV light produced by these circular reflector designs never reaches the water carrying conduits. Rather, a significant portion of reflected light is reabsorbed by the UV bulb assembly and never reaches the water carrying conduit.

A third problem involves the electrical coupling of the lamp assemblies to WTS units. Every time a lamp assembly is installed in or removed from a WTS unit, the lamp assembly must be mechanically and electrically coupled and uncoupled relative to the WTS unit. This often required complicated and expensive electrical mounting assemblies. Further, care must be taken to insure that the electrical connections are not exposed to moisture while electrical power is passing through the WTS unit.

Coaxially aligned lamp assemblies and filter assemblies are sometime used to minimize the size of WTS units. A lamp assembly and filter assembly in a particular WTS may or may not be simultaneously removed from the WTS unit. If these assemblies are simultaneously removed, they are often very quite heavy as they may have substantial weight on their own and may be filled with water. Alternatively, even if the lamp and filter assemblies are separably removably from a WTS unit, quite often problems exist of water spilling from one of these assemblies during handling.

Another problem faced by WTS units having UV lamp assemblies is that complicated monitoring systems are needed to monitor the lamp assemblies. As a lamp assembly ages, the intensity of UV light output from the lamp assembly generally diminishes. Eventually, the intensity falls below a level necessary to effect a desired microorganism kill rate. The lamp assembly should be replaced before the desired minimum intensity is reached. Accordingly, a monitoring system is required to check on the UV light intensity within the WTS unit. These monitoring systems are typically expensive. They often require costly UV light sensors with quartz windows.

Point-of-use water treatment systems are typically left running continuously due to microorganism growth that would otherwise occur if the systems were shut down. Lamp assemblies in typical WTS units require a relative long time to reach a threshold value of emitted radiation intensity needed to attain a desired kill rate. Accordingly, water containing unacceptably high levels of live microorganisms may be delivered from a WTS unit before that threshold value of light intensity is reached.

Other problems and deficiencies that typical WTS units have include complicated assembly and locking mechanisms for mounting filter and lamp assemblies which may include nuts, bolts and O-rings which must be manually installed.

These and other deficiencies in prior WTS units employing lamp assemblies and filter assemblies are overcome by the present invention.

SUMMARY OF THE INVENTION

The present invention includes a point-of-use water treatment system which has a base unit, a filter assembly with an inner sleeve and a secondary water treatment device such as a UV lamp assembly. The inner sleeve provides a chamber for the secondary water treatment device. Ideally first and second valves and seals provide control of the flow of water between the filter assembly and the secondary water treatment device and between the secondary water treatment device and the base unit. The valves and seals prevent unwanted water spillage when the filter assembly and lamp assembly are removed and replaced from the base unit.

The present invention also includes a lamp assembly, preferably for use in a water treatment system that includes a bulb assembly, a reflector assembly and a conduit carrying water through the lamp assembly. The reflector assembly is configured or shaped to reflect and focus light emitted from the bulb assembly onto the conduit and away from returning to the bulb assembly thereby enhancing the efficiency of the lamp assembly.

The present invention further includes a replaceable lamp assembly, which includes a water-carrying conduit captured between a pair of ends caps and a bulb assembly for irradiating the conduit. The conduit serves as a reactor vessel in which microorganism and other contaminants may be treated. Enclosures may be used which cooperate with the end caps to form a generally closed vessel surrounding the UV bulb assembly and conduit. The lamp assembly may also include two or more conduits extending between the end caps. The lamp assembly is generally self-contained and can be readily installed in a test fixture or in the water treatment system.

Another aspect of the present invention is the use of condensing element to cool an intermediate portion of a bulb assembly between its filaments. The intermediate portion, which is cooled, allows a condensable material, such as mercury, to condense onto the intermediate portion of the bulb between filaments. When the lamp assembly is energized, the condensed mercury can quickly be revaporized as it lies in the arc path between the filaments. Otherwise, when the condensed mercury is located outside the arc path, the condensed mercury requires a greater time to become fully vaporized when the lamp assembly is reenergized. This condensing of the mercury in the arc path assists the lamp assembly in reaching a threshold intensity level in a shorter period of time. A condensing element extending between the bulb and a conduit carrying cool water can serve as a heat sink to cool the intermediate portion of the bulb in contact with the condensing element. If the condensing element is elastomeric, the condensing can also serve a cushioning functioning.

Yet another feature of the present invention is the use of a plastic light pipe impregnated with a florescent dye to convert UV light into visible light. This conversion allows the relative intensity of the UV light produced by a lamp assembly to be easily measured by an inexpensive visible light detector. The light pipe may include polished and angled surfaces to receive incident UV light and cause the light pipe to emit visible light at a particular emitting surface wherein the visible light may be measured for intensity. Preferably, the florescent dye is in the green wavelength of color.

An additional feature is the use of an inductively coupled base unit and lamp assembly to provide UV radiation necessary to kill microorganism passing through a water treatment system. Also, radio frequency identification (RFID) and communication between smart chips on the base unit, filter assembly and lamp assembly can provide information regarding operation of the water treatment system such as filter and lamp life and usage, identification of a particular filter assembly or lamp assembly, and other desired information. The use of inductive coupling and RFID allows the filter assembly and lamp assembly to operate without any hard wiring to a base unit. The base unit will include microprocessors to control the operation of the water treatment system.

It is an object of the present invention to provide a WTS unit which requires no direct physical electrical connection between a removable lamp assembly and a base unit which powers the lamp assembly.

It is another object to provide a WTS unit having a base unit with a primary coil and a lamp assembly with a secondary coil, the primary coil supplying energy to the secondary coil to power the lamp assembly such that a high intensity UV light is produced within the WTS unit.

A further object is to provide a reflector assembly in a WTS unit wherein the UV light produced by a UV bulb assembly is reflected and focused upon one or more conduits carrying water to be treated while minimizing reflected light striking and being absorbed by the UV bulb assembly.

It is an additional object to provide a WTS unit wherein a filter assembly cooperatively mounts to a base unit and to a lamp assembly to allow water to pass through the filter assembly and wherein when the filter assembly is removed from the base unit and lamp assembly, the filter assembly is self-sealing preventing water from spilling from the filter assembly.

Yet another object is to provide a WTS unit having a ballast and lamp assembly wherein a UV bulb assembly, upon start up, can virtually instantaneously produce UV light of sufficiently high intensity such that the lamp assembly can be run intermittently while maintaining desired microorganism kill rates.

Still yet another object is to provide a WTS unit which runs intermittently and has a UV bulb assembly with a pair of spaced apart filaments and a heat sink in contact with the UV bulb assembly such that a cool spot on the UV bulb assembly is formed between the filaments wherein at least one of the ionized gases will condense adjacent the cool spot between the filaments when the UV bulb assembly is deenergized. This allows the condensed gas to be quickly reionized when the UV bulb assembly is reenergized.

Still yet another object is to provide a light pipe which receives UV light, fluoresces and outputs visible light generally linearly proportional in intensity to the incoming UV light.

An additional object is to provide smart chips in one or more of filter and lamp assemblies which transponds with an electrical assembly on a base unit to record usage information from the filter and lamp assemblies.

BRIEF DESCRIPTION OF THE DRAWINGS

These and other features, objects, and advantages of the present invention will become readily apparent from the following description, pending claims, and accompanying sheets of drawings where:

FIG. 5 is an exploded perspective view of major components of the WTS unit;

FIGS. 13A-C are a perspective view of a secondary coil, a top plan view of a spool and a sectional view of the spool taken along line 13C-13C of FIG. 13B;

FIG. 14 is a perspective view of smart chip;

FIGS. 15A-B are a rear perspective view and a rear elevational view of a light pipe;

FIG. 16 is an exploded perspective view of a top support assembly;

FIG. 17 is a bottom perspective view of a top cap;

FIG. 18 is a top perspective view of a top shield;

FIG. 19 is an exploded perspective view of a lamp assembly;

FIGS. 20A-B are inside and side elevational views of an enclosure;

FIGS. 35A-B are a front perspective view and top plan view of a top shroud assembly;

FIGS. 36A-D are a front perspective view, a front elevational view, a sectional view taken along line 36C-36C of FIG. 36B, and a top plan view of the top shroud;

BEST MODE(S) FOR CARRYING OUT THE INVENTION

Figure 1:
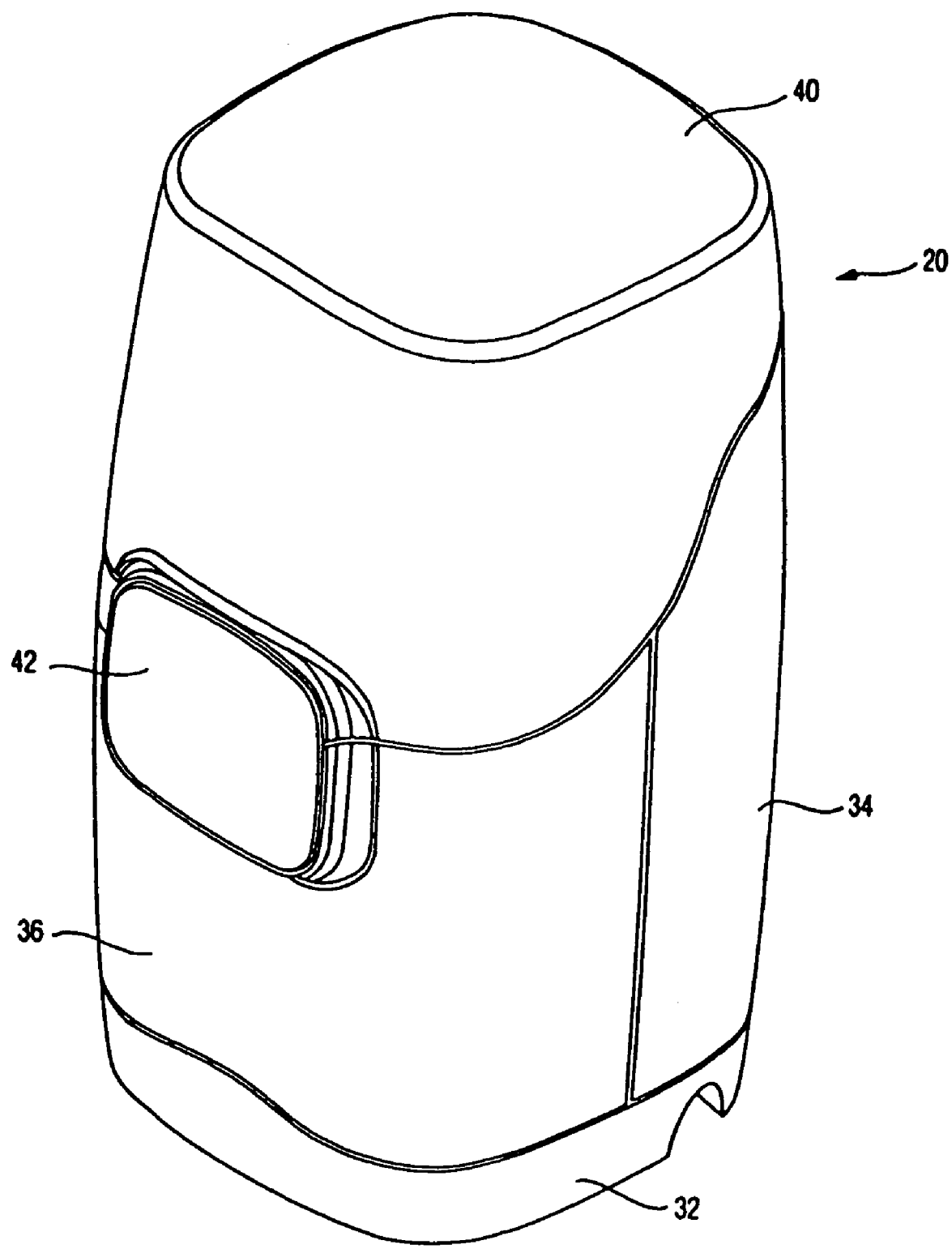
FIG. 1 is a perspective view of a WTS unit, made in accordance with the present invention.
Figures 2, 3:
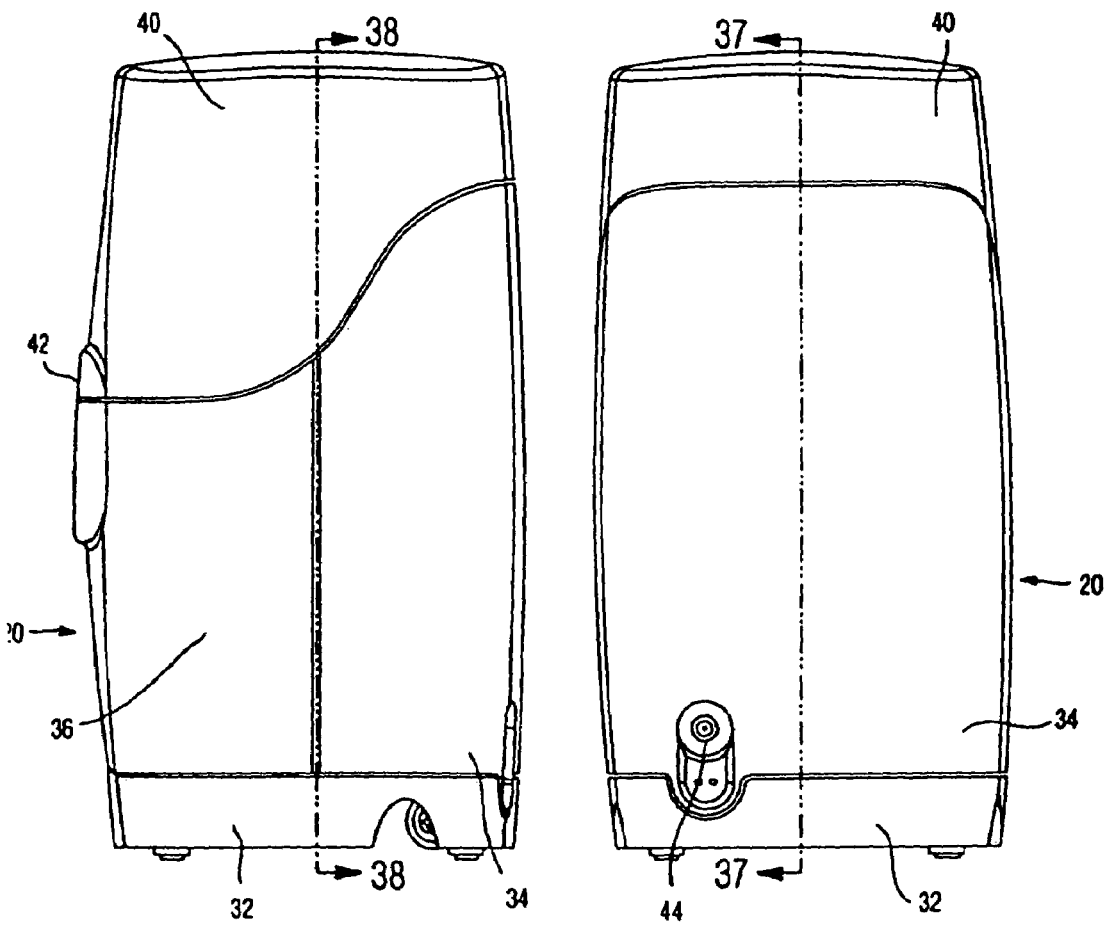
FIG. 2 is a left side elevational view of the WTS unit.
FIG. 3 is a rear elevational view of the WTS unit.
Figure 4:
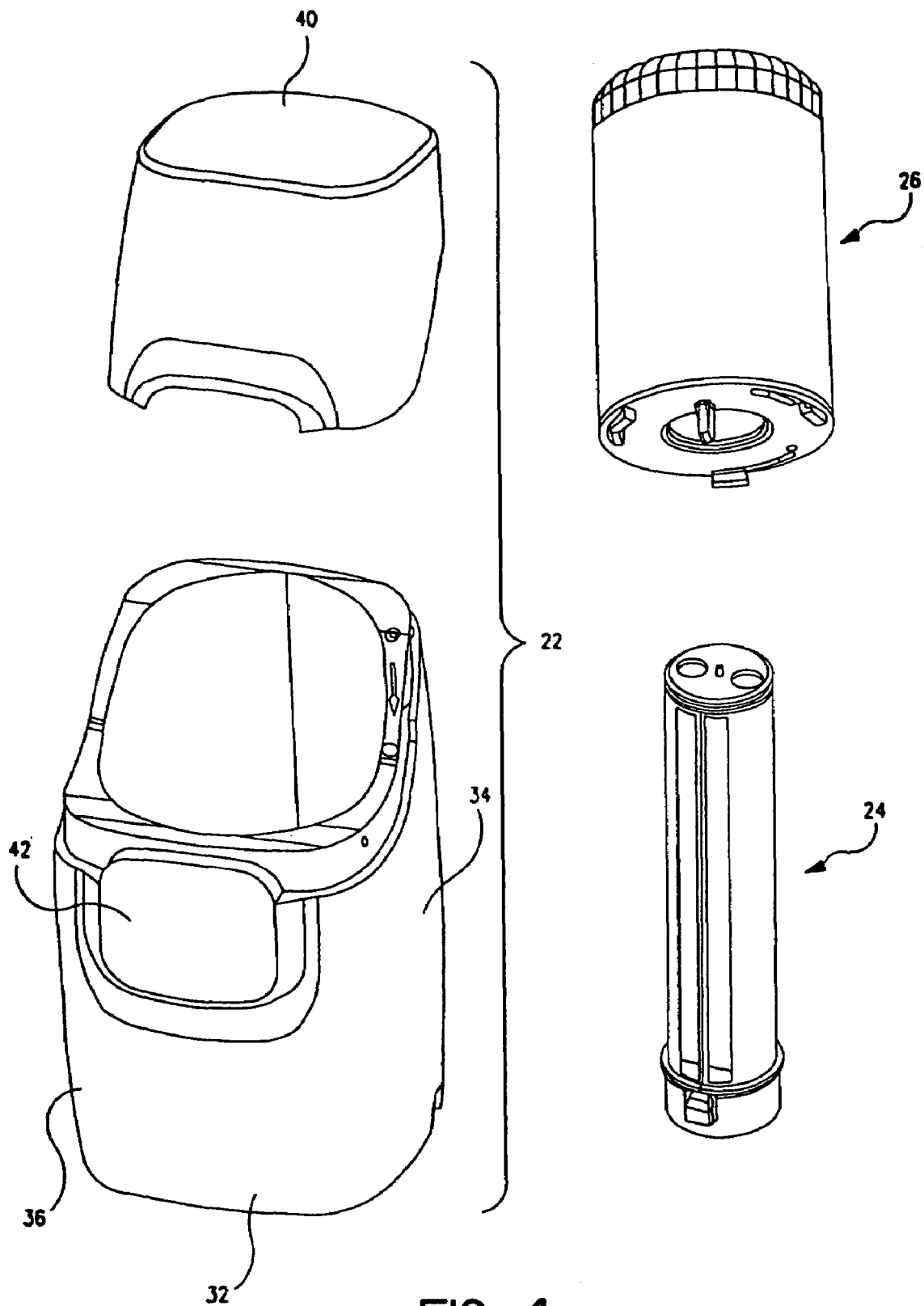
FIG. 4 is a perspective view of a base unit of the WTS unit with its top shroud removed and a filter assembly and a lamp assembly removed from the base unit.

An exemplary water treatment system (WTS) unit 20, made in accordance with the present invention, is shown in perspective view in FIG. 1. FIGS. 2 and 3 show respective left side and rear views of WTS unit 20. FIG. 4 illustrates an exploded view of major subcomponents of WTS unit 20 including a base unit 22, a lamp assembly 24 and a filter assembly 26. Lamp assembly 24 and filter assembly 26 are individually removable and replaceable from base unit 22. Filter assembly 26 is first removed from base unit 22 and then lamp assembly 24 can be dismounted from base unit 22. Similarly, lamp assembly 24 is first mounted to base unit 22. Then, filter assembly 26 is coaxially placed over lamp assembly 24 and bayonet mounted to base unit 22 when WTS unit 20 is being reassembled.

Referring now to FIGS. 1-3, the exterior of WTS unit 20 is formed by a bottom shroud 32, a back shroud 34, a front shroud 36 and a top shroud 40. A lens 42 is mounted in an opening in front shroud 36. Lens 42 accommodates the visual display of operating parameters of WTS unit 20. FIG. 2 shows a left side elevational view and FIG. 3 shows a rear elevational view of WTS unit 20. A power plug assembly 44 for receiving power is located in the rear of back shroud 34. FIG. 4 demonstrates that top shroud 40 is first removed before filter assembly 26 and then lamp assembly 24 are removed from the rest of base unit 22.

Turning now to FIG. 5, major components of WTS unit 20 are shown in perspective view. Base unit 22 includes an inner sleeve 50 with three inner sleeve covers 52, an inlet valve assembly 54, an outlet cup assembly 56 with outlet cup 58, a bottom shroud assembly 60 including bottom shroud 32 along with inlet and outlet elbow assemblies 62 and 64, and an electronics assembly 66. These components are enclosed within bottom shroud 32, front shroud 36 and lens 42, back shroud 34 and top shroud 40. Also shown are a magnet holder 68 and a magnet 70 which attach to top shroud 40. If top shroud 40 and magnet 70 are not properly positioned atop the remainder of WTS unit 20, the magnetic field of magnet 70 is not sensed by a sensor on electronics assembly 66 and WTS unit 20 cannot be energized.

Lamp assembly 24 includes base subassembly 72, secondary coil 74, bottom support subassembly 76, top support assembly 78, a pair of quartz sleeves 80, a UV bulb assembly 82 and a pair of cooperating enclosure and reflector subassemblies 86. Filter assembly 26 comprises a filter block assembly 88, including a filter block 90, a base and inner sleeve 92, a thread ring 94, a filter housing 96, and an elastomeric filter housing grip 98.

The aforementioned components will now be described individually in greater detail. Then, the assembly and mating of the various components will be described utilizing a variety of sectional views through WTS unit 20.

A. Filter Assembly

Referring to FIGS. 6A-E, filter assembly 26 includes filter block assembly 88, domed and cylindrical shaped outer filter housing 96, an inlet check ball 100, an outlet check ball 102, base and inner sleeve 92, filter thread ring 94, a block gasket 104 and filter housing grip 98. Filter housing grip 98 is elastomeric and is made of rubber in this exemplary embodiment. Filter housing grip 98 is stretched over and is frictionally mounted upon the upper domed end of outer filter housing 96. Filter block assembly 88 has annular carbon block 90 captured between a bottom filter end cap 106 and a top filter end cap 108. Filter block assembly 88 also has a carbon blanket 110 which surrounds the outer periphery of carbon block 90. Carbon blanket 110 is comprised of a nylon mesh which serves to filter or capture any large particles attempting to pass radially inwardly through carbon block 90. A smart chip 112 is held in the base of base and inner sleeve 92. Smart chip 112 is used to record parameters related to filter usage. A sensor on electronics assembly 66 inductively powers and communicates with smart chip 112 to obtain details on filter usage.

Figure 6E:
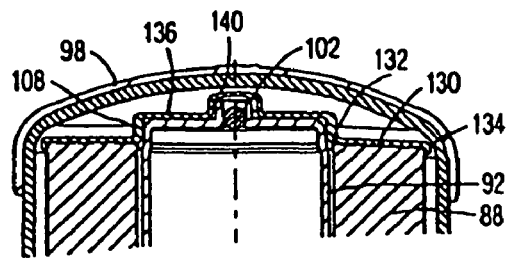
FIGS. 6A-E are an exploded view, an elevational view, a sectional view take along line 6C-6C of FIG. 6B, an enlarged fragmentary view taken from encircled area designated 6D in FIG. 6C, and an enlarged fragmentary view taken from encircled area designated 6E in FIG. 6C of the filter assembly.
Figure 6A:
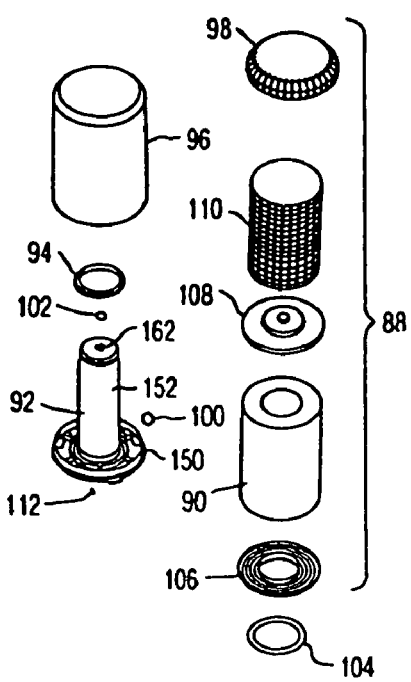
Figure 6D:
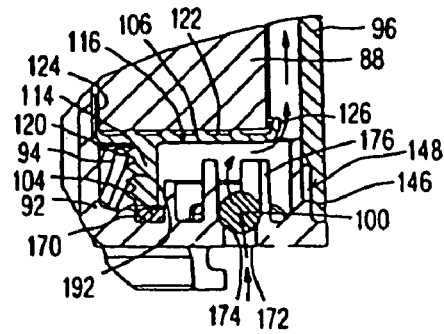
Figure 6B:
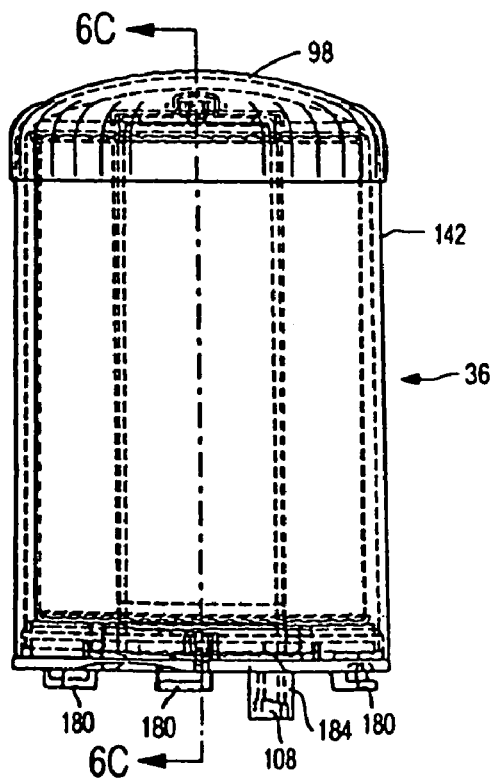
Figure 6C:
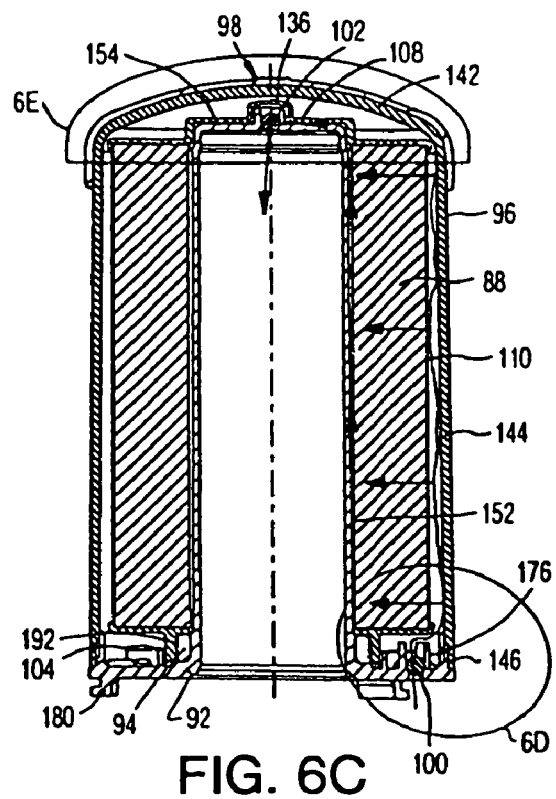
Figure 7A:
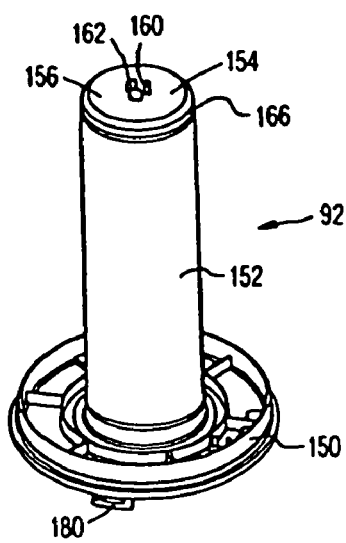
FIGS. 7A-F are a top perspective view, a bottom perspective view, a front elevational view, a sectional view taken along line 7D-7D of FIG. 7C, a top plan view and a bottom plan view of a base and inner sleeve.
Figure 7B:
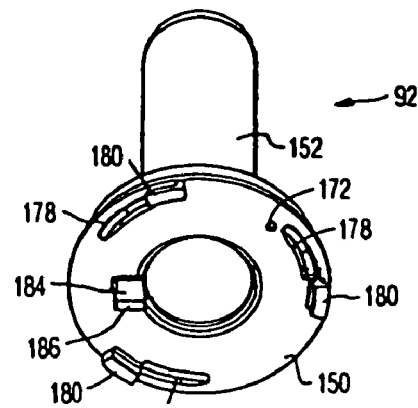
Figure 7C:
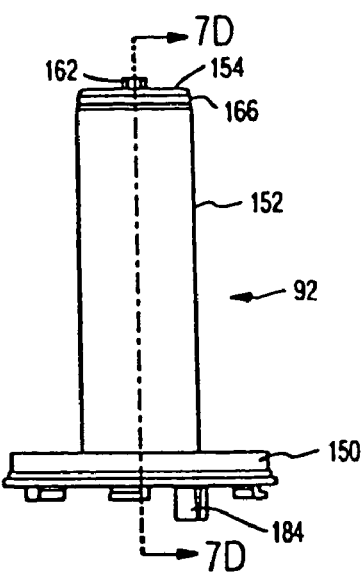
Figure 7D:
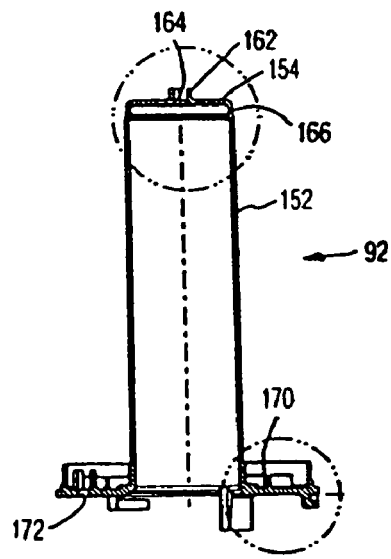
Figure 7E:
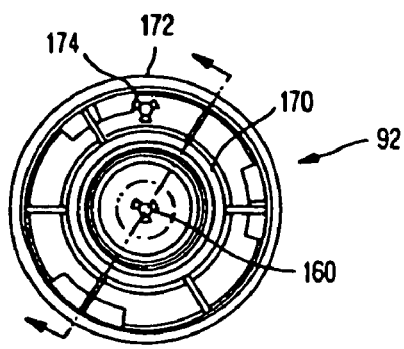
Figure 7F:
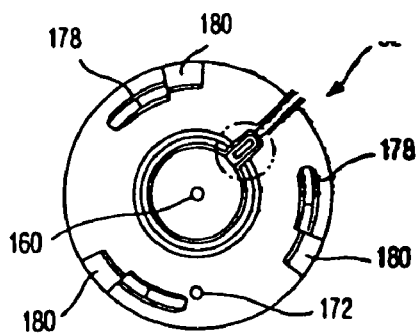

Looking to FIGS. 6C-D, filter block assembly 88 is disposed within filter housing 96 and rests upon block gasket 104 and the lower portion of base and inner sleeve 92. Block gasket 104 is retained in a groove in base and inner sleeve 92. Carbon block assembly 88 is threaded on to filter thread ring 94. In turn, filter thread ring 94 is permanently affixed, through a welding procedure, to base and inner sleeve 92. At its open end, outer filter housing 96 is welded to the outer periphery of base and inner sleeve 92. Inlet check ball 100 is slidably retained near the base of base and inner sleeve 92 while outlet check ball 102 is slidably retained atop base and inner sleeve 92 and beneath top end cap 108 of filter block assembly 88.

Looking to FIG. 6D, bottom filter end cap 106 has an annular hub portion 114 supporting a horizontally extending annular tray portion 116. Internal threads 120 are formed on the radially interior surface of hub portion 114. Tray portion 116 has a series of four concentric grooves 122 formed therein and also has inner and outer flanges 124 and 126. The bottom portion of carbon block 90 is supported upon tray portion 116 and is captured between inner and outer flanges 124 and 126. Referring now to FIG. 6E, top filter end cap 108 includes an annular tray portion 130 having inner and outer flanges 132 and 134, an annular cap portion 136 and a downwardly opening ball retaining cup portion 140. Although not clearly shown, tray portion 130 also includes four concentric grooves which are disposed opposing carbon block 90. Upper end cap 108 is configured to slidably capture outlet check ball 102 atop the upper portion of inner sleeve 92.

Filter housing 96 includes a closed domed end portion 142 and a cylindrical portion 144. At the open end of cylindrical portion 144 is a reduced thickness end portion 146 which is designed to be permanently attached to base and inner sleeve 92, as shown in FIGS. 6C-D. EMA tape 148 is located in a gap formed between end portion 146 and the outer periphery of base and inner sleeve 92 to facilitate welding.

Base and inner sleeve 92 is shown individually in FIGS. 7A-F. Base and inner sleeve 92 includes a base portion 150, an intermediate cylindrical portion 152, and a top portion 154. Top portion 154 includes a disk like end cap 156 with an outlet opening 160 extending therethrough. Three circumferentially spaced arcuate projections 162 surround outlet opening 160 and serve to surround and position outlet check ball 102. Around the periphery of outlet opening 160 is a ball seat 164. The upper end of cylindrical portion 152 includes a stepped portion 166 which is configured to engage with a corresponding portion of lamp assembly 24 (not shown).

As best seen in FIG. 6D, base portion 150 includes a gasket groove 170 for receiving block gasket 104, an inlet opening 172 surrounded by a ball seat 174 and three cooperating and circumferentially spaced apart projections 176 which guide inlet check ball 100. Returning to FIGS. 7A-D, three circumferentially spaced apart ramped scallops 178 and L-shaped retaining tangs 180 are formed on the bottom of base portion 150 to allow filter assembly 26 to be bayonet mounted to inner sleeve 50. Ramped scallops 178 assist in lifting filter assembly 26 away from base unit 22 when filter assembly 26 is disconnected from base unit 22. A rectangular-shaped smart chip retainer chamber 184 having an opening 186 therein is also formed on the bottom of base portion 150. Opening 186 is sized to hold smart chip 112 in an interference or press fit. Smart chip 112 serves the purpose of recording and transmitting information to electronics assembly 66.

Filter thread ring 94 includes exterior threads 192. The interior radial periphery of filter thread ring 94 is sized to mate with the outer diameter of cylindrical portion 152 of base and inner sleeve 92. Filter thread ring 94 is sonically welded to cylindrical portion 152 of base and inner sleeve 92 adjacent base portion 150, as shown in FIGS. 6C and D.

Filter assembly 26 is assembled as follows. Filter thread ring 94 is placed over cylindrical portion 152 of base and inner sleeve 92 adjacent base portion 150. Sonic welding is used to permanently attach filter thread ring 94 to cylindrical portion 152. Inlet check ball 100 is set within cooperating projections 176 resting upon ball seat 174. Similarly, outlet check ball 102 is positioned within projections 162 upon ball seat 164. Block gasket 104 is positioned within gasket groove 170 of base portion 150 of base and inner sleeve 92. Cylindrical portion 152 of base and inner sleeve 92 is then slipped within the inner radial periphery of filter block assembly 88. Outlet check ball 102 is thus captured within projections 162 and beneath cup portion 140 of top end cap 108 of filter assembly 26. Filter block assembly 88 is then threaded onto filter thread ring 94 compressively capturing gasket 104 between filter block assembly 88 and base and inner sleeve 92. Filter housing 96 is placed over filter block assembly 88 resting upon base portion 150. End portion 146 of filter housing 96 is (EMAWELD) welded to the radial exterior of base portion 150 utilizing EMA tape 148 thus creating a closed pressure vessel or filter assembly 26. Smart chip 112 is pressed into retainer chamber 184.

During operation of WTS unit 20, water travels through filter assembly 26 along he pathway shown by arrows in FIGS. 6C-D. Pressurized water is introduced at filter inlet opening 172 lifting inlet check ball 100 from its ball seat 174. (Note that water cannot pass backwards from filter assembly 26 through filter inlet opening 172 as inlet check ball 100 and ball seat 174 form a one-way check valve.) Water fills the annular region formed beneath bottom filter end cap 106 of filter block assembly 88 and above base portion 150 of base and inner sleeve 92. Next, water passes upwardly to the annular region created between the radial exterior of carbon block 90 and the interior of filter housing 96. Water enters the outer diameter of carbon block 90 and is filtered as the water passes to its radial interior periphery.

Water is then received in the annular space created between carbon block 90 and cylindrical portion 152 of base and inner sleeve 92. Water must then pass upwardly over top portion 154 of base and inner sleeve 92 and beneath cap portion 136. Outlet check ball 102 is seated in ball seat 164 and prevents water from exiting filter assembly 26 unless outlet check ball 102 is displaced upwardly. This occurs only when filter assembly 26 is properly positioned over lamp assembly 24 as will be described later. When filter assembly 26 is removed from base unit 22 and lifted from lamp assembly 24, outlet check ball 102 will seat in ball seat 164 and water held in filter assembly 26 will remain within filter assembly 26.

B. Lamp Assembly

Figures 8A, 8B, 8C:
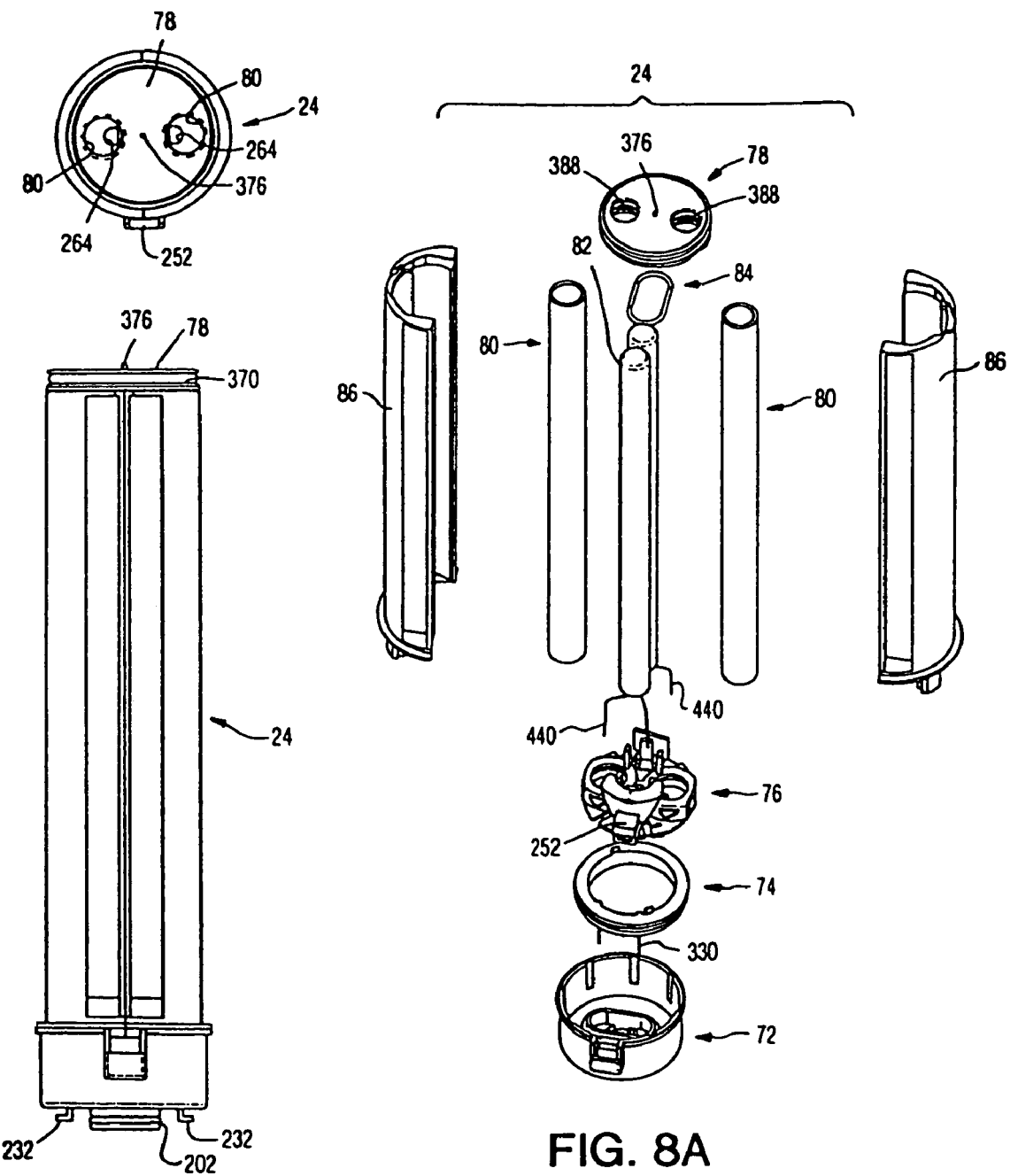
FIGS. 8A-C are an exploded perspective view, an elevational view, and a top plan view of a lamp assembly.

FIGS. 8A-C show lamp assembly 24. Lamp assembly 24 includes base subassembly 72, secondary coil 74, bottom support subassembly 76, top support assembly 78, a pair of quartz sleeves 80, a UV bulb assembly 82, condensing O-ring 84 and a pair of cooperating enclosure and reflector subassemblies 86.

Figure 9A:
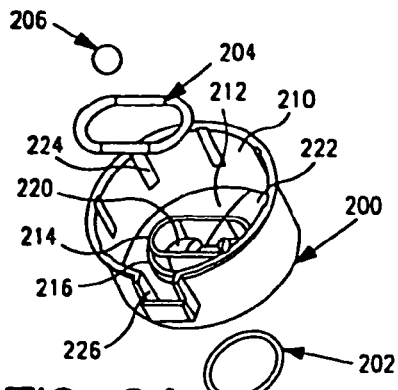
FIGS. 9A-C are an exploded perspective view, a top plan view and a sectional view taken along line 9C-9C of FIG. 9B of a base assembly of the lamp assembly.
Figure 9B:
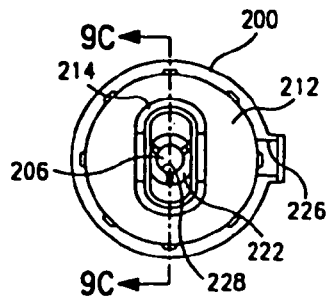
Figure 9C:
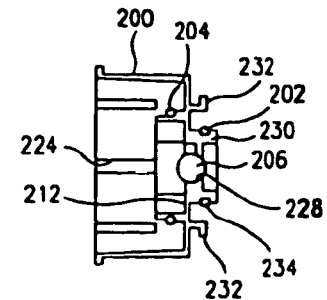

FIGS. 9A-C illustrate base subassembly 72. Base subassembly 72 includes a cup shaped base 200, an outlet O-ring 202, an oval manifold seal 204 and a check ball 206. Base 200 has a cylindrical wall 210 and a base wall 212. An oval wall 214 extends upwardly from base wall 212 and has on its outer surface an oval seal step 216. Located within oval wall 214 is a bottom wall 220 with a pocket 222 therein for receiving check ball 206. Alignment grooves 224 extend vertically along the inside of cylindrical wall 210. Located on cylindrical wall 210 is a light pipe pocket 226. An outlet opening 228 is formed in a hub 230 disposed below base wall 212. A pair of L-shaped bayonet members 232 are formed beneath base wall 212. Bayonet members 232 serve to releasably retain lamp assembly 24 to outlet cup 58 when WTS unit 20 is assembled. A groove 234 is formed in the outside of hub 230 to accommodate outlet O-ring 202. Oval manifold seal 204 rests upon oval seal step 216.

Figure 37:
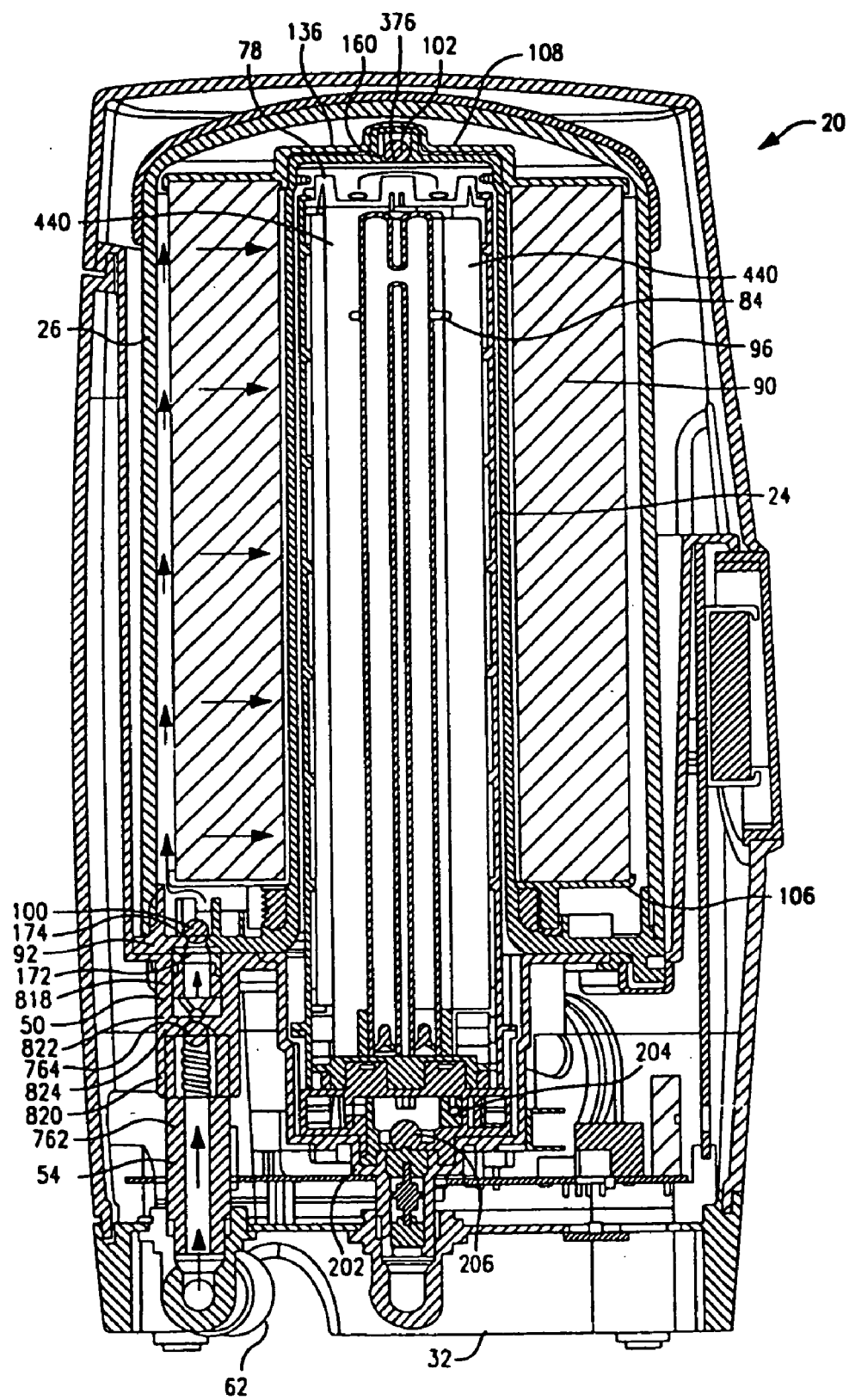
FIG. 37 is an enlarged sectional view taken along line 37-37 of FIG. 3 of the WTS unit.
Figure 38:
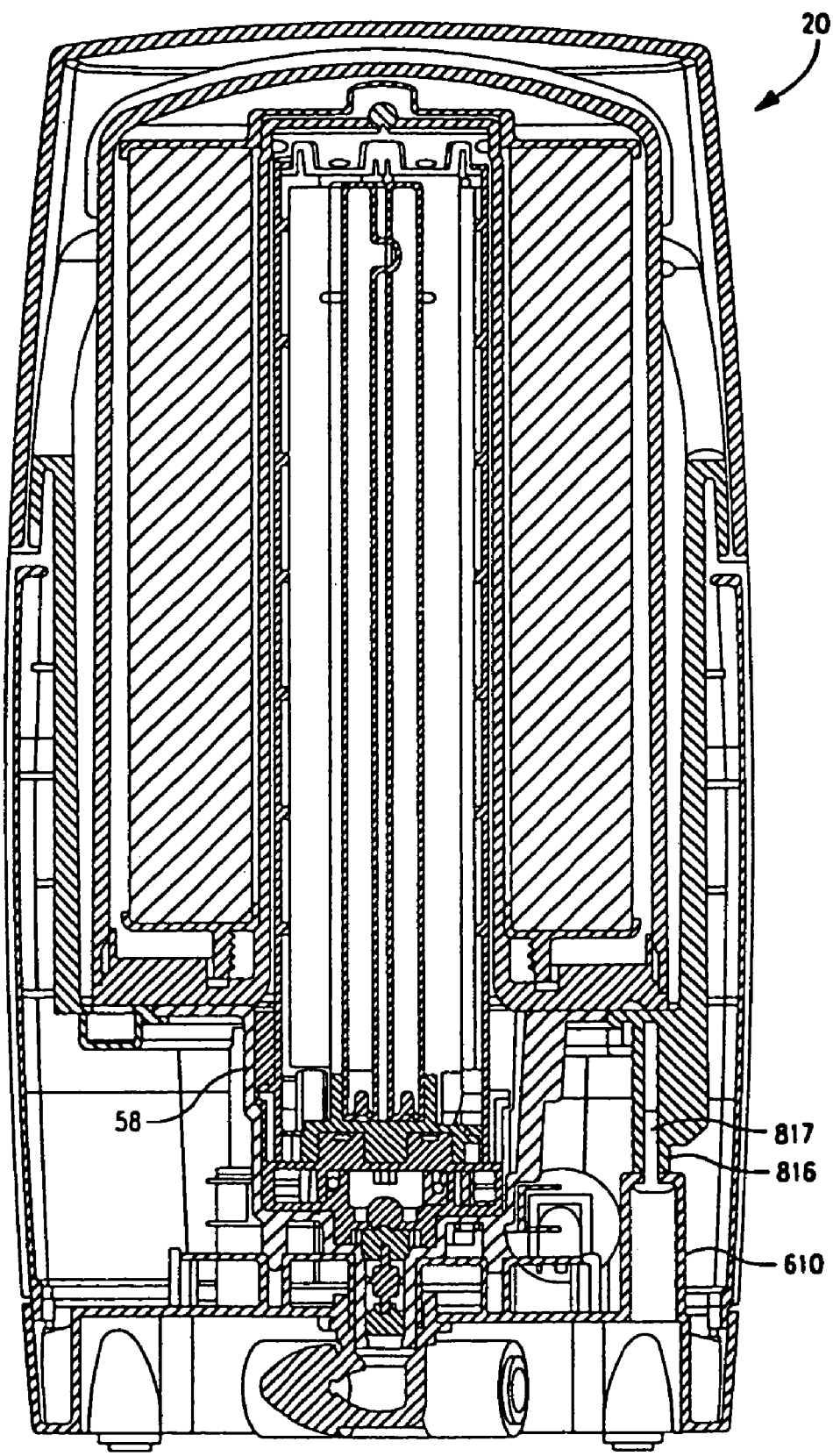
FIG. 38 is an enlarged sectional view taken along line 38-38 of FIG. 2.

Check ball 206 prevents water from escaping from lamp assembly 24 when UV lamp assembly 24 is removed from base unit 22. Oval manifold seal 204 serves to seal between base subassembly 72 and bottom support assembly 76, as best seen in FIGS. 37 and 38. Outlet O-ring 202 seals between base subassembly 72 and the inside of outlet cup 58.

Figure 10B:
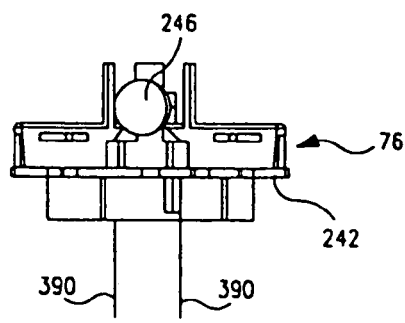
FIGS. 10A-E are an exploded perspective view, an elevational view, a bottom plan view, a side elevational view and a top plan view of a base subassembly of the lamp assembly.
Figure 10A:
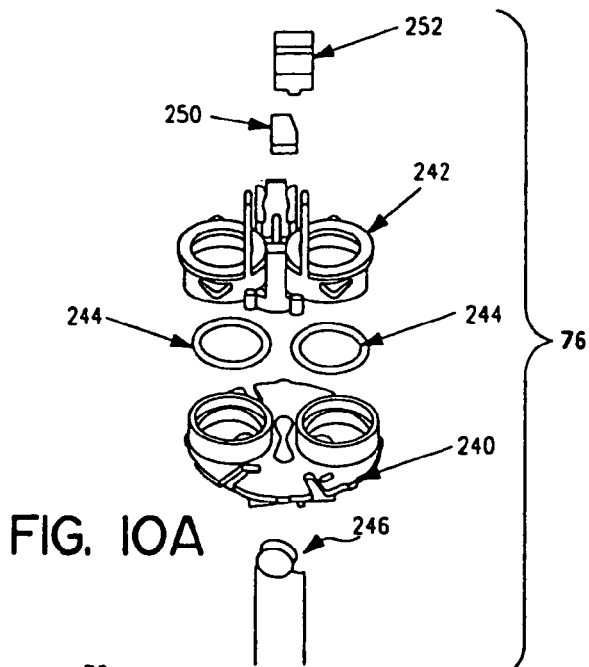
Figure 10C:
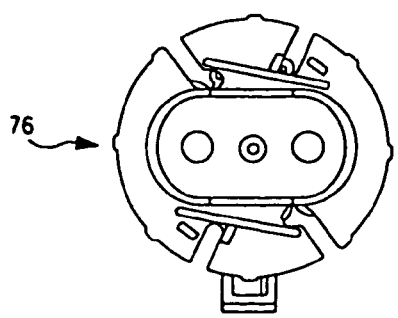
Figure 10D:
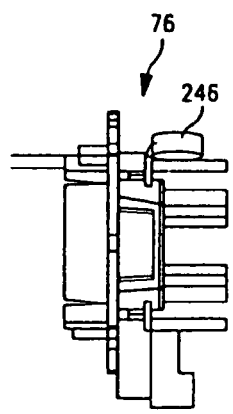
Figure 10E:
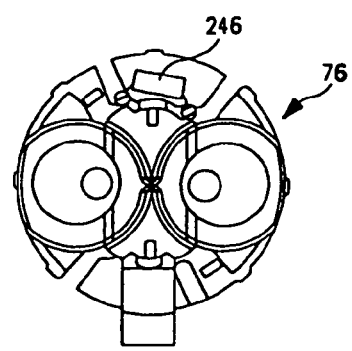

Bottom support assembly 76 is shown in exploded view in FIG. 10A and assembled in FIGS. 10B-10E. A base support 240 cooperates with a bottom shield 242 to capture about a pair of O-rings 244. A thermistor 246 attaches to bottom shield 242. A smart chip 250 and a light pipe 252 are held within bottom support assembly 76, as will be described in more detail below. Smart chip 250 electronically communicates with electrical assembly 66. Smart chip 250 measures various operating parameters of lamp assembly 24. Light pipe 252 converts UV light from within lamp assembly 24 to visible light which is sensed by a light sensor on electronics assembly 66. Thermistor 246 operates to sense temperature within lamp assembly 24. Alternatively, separate temperature sensing circuitry may be used to control the temperature within WTS unit 20. WTS unit 20 will automatically turn on to prevent freezing of water within WTS unit 20.

Figure 11A:
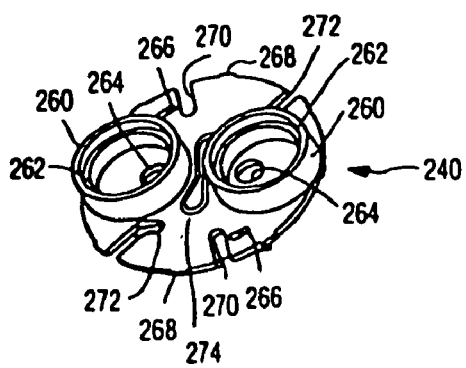
FIGS. 11A-C are a perspective view, a top plan view and a bottom plan view of a base support of the base subassembly.
Figure 11B:
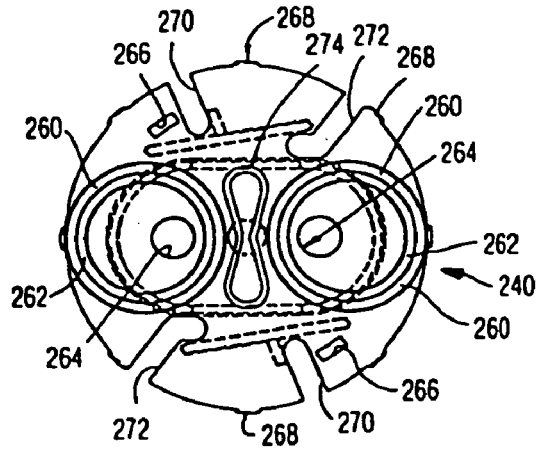
Figure 11C:
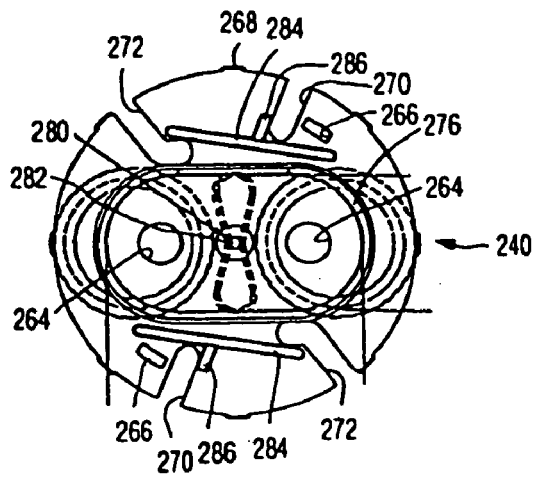

Base support 240 is shown in FIGS. 11A-C. A pair of bottom cups 260 each have an O-ring seat 262 to retain an O-ring 244. At the bottom of each of cups 260 is a water outlet opening 264. A pair of rectangular bayonet openings 266 are used to secure secondary coil 74 beneath base support 240. Eight alignment ribs 268 are formed on the outer peripheral edge to align base support 240 within grooves 224 of base 200. Located at the outer periphery of base support 240 are a pair of U-shaped slots 270 and L-shaped slots 272. A bow-tie shape support 274 is formed at the center of base support 240 and serves as an energy diverter feature for sonically welding bottom shield 242 to base support 240. As best seen in FIG. 11C, an oval wall 276 is disposed on the bottom of base support 240 and is used to interface with and about oval wall 214 on base assembly 72 (FIG. 9A). At the center is a support structure 280 having a pilot aperture 282. Two pairs of long and short locating ribs 284 and 286 form a T-configuration. The free ends of ribs 284 and 286, along with the ends of oval wall 276 serve to pilot the inner radial circumference of secondary coil 74.

Figure 12A:
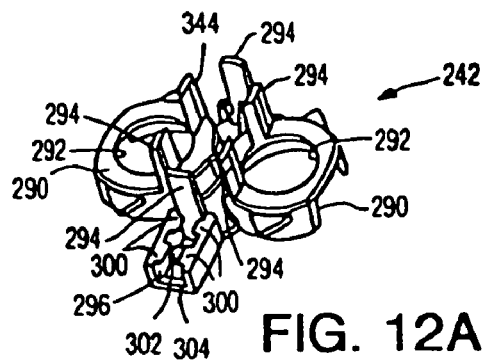
FIGS. 12A-C are a perspective view, a top plan view and a bottom plan view of a bottom shield of the base subassembly.
Figure 12B:
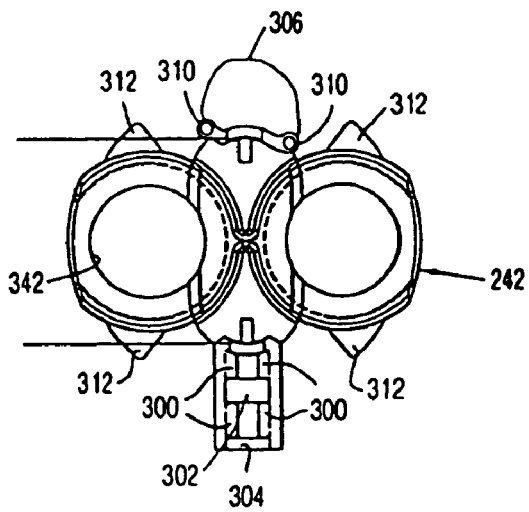
Figure 12C:
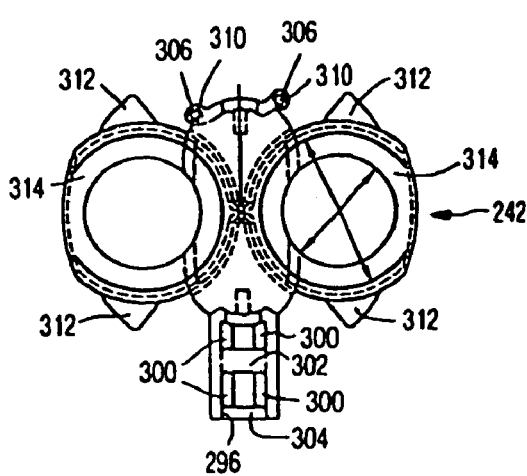

Bottom shield 242 is shown individually in FIGS. 12A-C. A pair of top cups 290 are configured to oppose bottom cups 260 on base support 240 with O-rings 244 being captured therebetween. Openings 292 in each of cups 290 are adapted to receive the lower ends of quartz sleeves 80 (FIG. 8A). Six upwardly extending ribs 294 are arranged in a generally oval manner to capture the lower end of UV bulb assembly 82 (FIG. 8A). A generally rectangular shaped pocket 296 is sized to receive smart chip 250 therewithin and also the dovetail base of light pipe 252 (FIG. 15B). Pocket 296 is defined on its top side by four inboard extending wedge shaped ribs 300. The ribs 300 cooperate to retain light pipe 252 in a dove-tail type mount. The bottom of pocket 296 is formed by intermediate and end cross-members 302 and 304. Wire openings 306 are formed in bosses 310 located on the opposite side of bottom shield 240 from pocket 296. Wire openings 306 accommodate the mounting of thermistor 246. Also, four triangular ribs 312 are formed on bottom shield 240 and serve to align enclosure subassembly 76. The undersides 314 of top cups 290 form a seat to retain O-rings 244 (FIG. 10A).

Secondary coil 74 is shown in FIG. 13A. Coil 74 includes an annular bobbin 320 which has a wire coil 326 wrapped thereabout. There are 55 turns on wire coil 326. Bobbin 320 includes a pair of diametrically spaced retaining tangs 322 and a pair of apertured bosses 324. A pair of lead wires 330 extend through apertured bosses 324. Retaining tangs 322 are designed to secure within tang openings 266 (FIGS. 11A-C) of base support 240 to secure secondary coil 74 beneath bottom support assembly 76 (FIG. 8A).

Smart chip 250 is shown in FIG. 14. Smart chip 250 has a main body 340 with a computer chip 342 imbedded or molded therein. Main body 340 includes a rectangular portion 344 and a wedge portion 346. Smart chip 342 is slid into pocket 296 with rectangular portion 344 being held in an interference fit and wedge portion 346 extending outboard.

Light pipe 252 is shown in FIGS. 15A and B. Light pipe 252 includes a curved portion 350 and a block shaped mounting portion 352. On the underside of mounting portion 352 is a wedge shaped dovetail portion 354. The dovetail portion 354 engages with the four wedged ribs 302 of pocket 296 (FIGS. 12A-C) to securely fasten light pipe 252 to bottom shield 242. Curved portion 350 includes a top face 360 which is polished and receives UV light from within lamp assembly 24. The UV light causes light pipe 252 to fluoresce and emit visible light which is reflected to pass out an outboard face 362 on light pipe 252. An inboard curved face 364 faces the base of UV bulb assembly 82 and actually receives relatively little UV light, as compared to top face 360, when lamp assembly 24 is operating. Light pipe 252 will be described in greater detail later in conjunction with the operation of lamp assembly 24.

FIG. 16 is an exploded view of top support assembly 78. Components of top support assembly 78 include a top cap 366, a top shield 368, an inlet O-ring 370 and a pair of quartz O-rings 372. Top cap 366 and top shield 368 are shown individually in respective FIGS. 17 and 18. Top cap 366 has a disk body 374 with a button 376 extending upwardly from its top side. Button 376 operates to unseat outlet ball 102 of filter assembly 26 when filter assembly 26 is placed over lamp assembly 24. Around the outer periphery is a flange 380 with a groove 382 for receiving inlet O-ring 370. Disposed on the underside of disk body 374 is a pair of top cups 384. Formed within top cups 384 are seal steps 386. Openings 388 extend through top cap 366. Top shield 368 has a circular main body 390 with recesses 392 formed therein which are adapted to cooperate with top cups 384. A pair of openings 394 extend through top shield-368. Quartz O-rings 372 are captured between top cups 384 and recesses 392 providing top support assembly 78 with a seal mechanism for sealing about the top ends of quartz sleeves 80 during assembly of lamp assembly 24.

FIG. 19 shows an exploded view of lamp assembly 24. FIGS. 20A-B show front and side views of an enclosure 400. Enclosure and reflector subassemblies 86 each include an enclosure 400 and a reflector-402. Enclosures 400 each include a curved center portion 404 connecting between a pair of planer portions 405. At the base of each enclosure 400 are a pair of L-shaped retaining tangs 406. Located along the longitudinal peripheries of each of enclosures 400 are flanges 407 having a series of pins 408 and mating holes 410. When pressed together, enclosures 400 mate with one another with opposing pins 408 and holes 410 cooperatingly fitting together. At the top of enclosures 400 are opposing lower and upper flanges 412 and 414 creating a lid receiving gap 416 therebetween. Gap 416 receives top support assembly 78 when lamp assembly 24 is assembled. A generally rectangular opening 420 is formed in the top of enclosure 400 to accommodate portions of elastomeric O-ring 370. At the base of each enclosure 400 is an outer flange 422 and an inner flange 424. Inner flanges 424 are designed to capture about bottom support assembly 76. Outer flanges 422 are received by base 200. Retaining tangs 406 are received within grooves on the inner surface of base 200. Enclosures 400 have a series of longitudinally spaced ribs 426 to enhance structural strength.

Figure 21A:
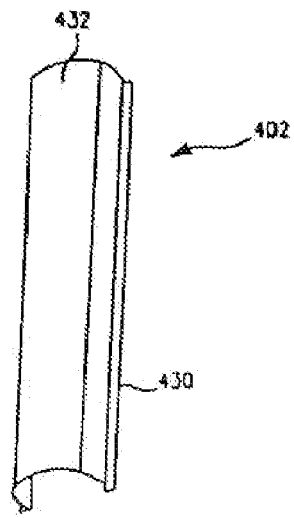
FIGS. 21A-B are perspective and top end views of a reflector.
Figure 21B:
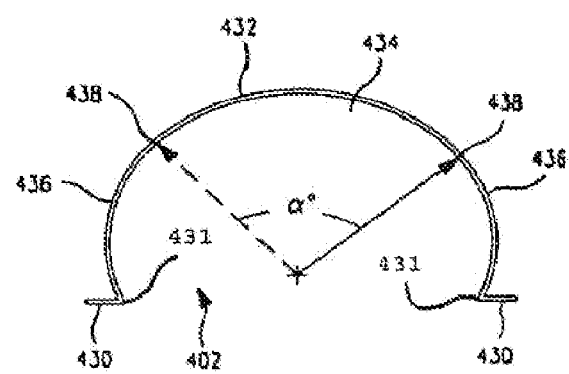

FIGS. 21A and B show an exemplary reflector 402. Reflector 402 is generally Omega shaped in cross-section have flanges 430 and a center curved portion 432. Curved portion 432 includes a constant radius portion 434 and a converging radius portion 436. Constant radius portion 434 extends over an angle α of approximately 90 degree. The radius of curvature over center curved portion 432 is constant. Meanwhile, the radius of curvature of converging radius portion 436 decreases from inflection points 438 to flanges 430. This decreasing radius of curvature 436 terminates and forms a curvature peak 431 that projects outward toward the longitudinal axis of the reflector before transitioning to the flange 430. As exemplified in FIG. 22, this curvature peak 431 can be located immediately adjacent the bulb 440.

Figure 22:
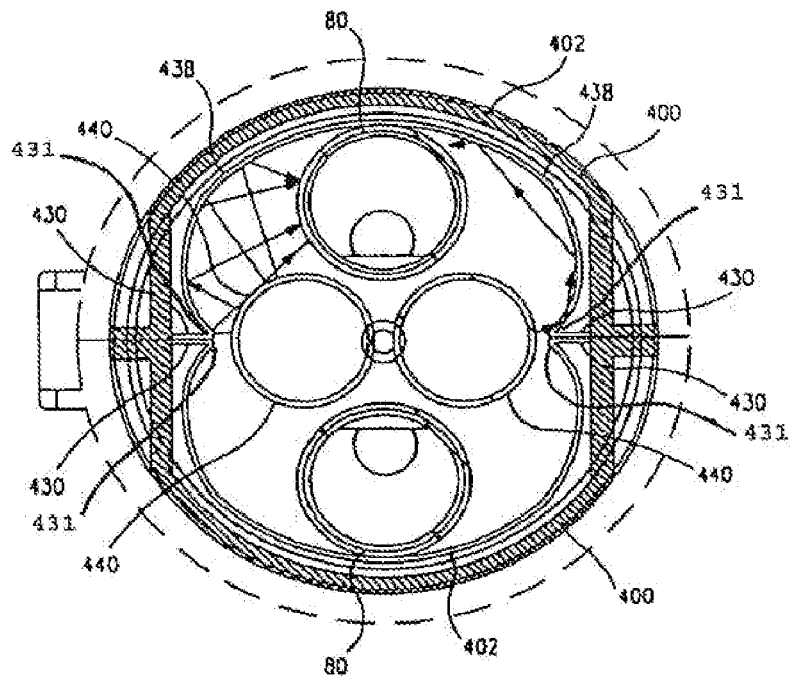
FIG. 22 is a sectional view through a lamp assembly showing exemplary reflected UV light rays.

As can be appreciated from FIG. 22, this Omega (Ω) shaped design of reflectors 402 enhances the focusing or reflecting of UV light rays upon quartz sleeves 80 while minimizing rays reflected or focused back upon bulbs 440 of UV bulb assembly 82. Light rays travelling perpendicular or normal from points on the surface of bulbs 440 will encounter the greatest angle of reflectance upon converging radius portion 436 adjacent flanges 430 with the angle of reflectance of the normal light rays decreasing moving toward inflection points 438. That is, the closer a portion of a bulb 440 is to reflector 402, the greater the angle of reflectance provided by reflector 402 to help normal light rays avoid returning to UV bulb assembly 82. Similarly, light rays which strike reflector 402 at an angle insufficient to bounce directly upon a quartz tube 80 will tend to strike another portion of reflector 402 one or more times and then strike a quartz sleeve 80 rather than striking one of the emitting bulbs 440. Use of these Omega shaped reflectors 402 is estimated to produce up to a 40% increase in lights ray intensity which strike quartz tubes 80 either directly or within the 3 reflections or bounces off the inside mirrored surfaces as compared to using reflectors which are completely circular in-cross sectional shape and encompass bulbs 440. Reflectors 402 are made of aluminum in this preferred embodiment with the insides of reflectors 402 being polished to enhance reflectivity. Reflectors 402 should be made of a material which reflects rather than absorbs light in the UV range of the electromagnetic spectrum. While it is preferred that reflector 402 have a generally smooth, continuous curved inner surface, it is also possible that a faceted reflector could also be used as long as the facets enhance the diversion or focusing of reflected light rays away from bulbs 440 and toward quartz tubes 80.

Figure 23A:
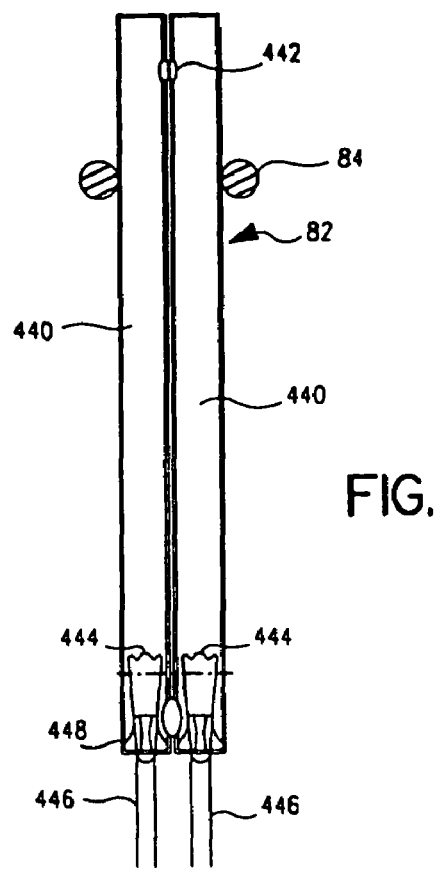
FIGS. 23A-D are an elevational view, and schematic upright, inverted and upright with heat sink views of a UV bulb assembly.

FIG. 23A shows UV bulb assembly 82. UV bulb assembly 82 comprises the two side-by-side emitting bulbs 440 with an upper passageway 442 which allows gases to pass between the two bulbs 440. A pair of filaments 444 is electrically connected to respective pairs of leads 446. Leads 446 pass through a base 448 of UV bulb assembly 82. Leads 436 are connected to secondary coil 74 to power lamp assembly 24. UV bulb assembly 82 is filled with a neon-argon (Ne—Ar) gas mixture in a most preferred ratio of 99:1. It is also envisioned that mixtures from a 50:50 mixture up to a 99.5-0.5 mixture will also work in the present invention. Also, mercury (Hg) is contained within bulbs 440 and is in a solidified state at room temperatures. The mercury is vaporized during operation of UV bulb assembly 82. The neon-argon gas mixture serves as a starter to assist in getting the mercury in a plasma state. Use of the neon-argon gas mixture produces a higher instant light output compared to conventional UV bulb assemblies using gases such as using greater than 50% argon. Also, the use of neon-argon mixture provides a higher overall stability with higher wall temperatures in bulbs 440 than found in conventional UV bulb assemblies. This is particular important in cold weather or cold operating conditions such as in the presence of cold running water through WTS unit 20. These features contribute to an improved intensity and shorter startup time as compared to previous UV bulb assemblies used in WTS units.

Energy delivered from one filament 444 arcs upwardly through passageway 442 and goes down to the other filament 444. In the process the gases are excited and light is produced. During cathode pre-heat, the filaments produce an orange-red ionization. As the neon-argon mixture starts to get excited, a red light is produced. Finally, the ionization of the neon-argon gas mixture forces the Hg to vaporize producing UV light of 254 nanometers in wavelength. It is the UV light which is most effective in destroying microorganisms passing through quartz sleeves 80 of lamp assembly 24.

Condensing O-ring 84 is used to cushion UV bulb assembly 82 from contact with quartz sleeves 80. O-ring 84 also acts as a heat sink drawing heat from bulbs 440 to quartz sleeves 80 through which relatively cool water passes during operation of WTS unit 20. After UV bulb assembly 82 has been initially excited and operated, the temperature of the portion of bulbs 440 directly in contact with O-ring 84 is slightly cooler than the adjacent other portions of bulbs 440. Accordingly, the vaporized mercury plasma tends to condense within bulbs 440 adjacent condensing O-ring 84 whenever lamp assembly 24 is shut off. Without the presence of the condensing O-ring 84, much more of the mercury would tend to condense at the base of lamp assembly 82 beneath filaments 444. It has been found that lamp assembly 24 can be brought up to a predetermined intensity level much quicker in the presence of condensing O-ring 84 than in its absence. This is because the mercury condenses in the arcing pathway between filaments 444 rather than beneath filaments 444 and outside of the arcing path.

Figure 23B:
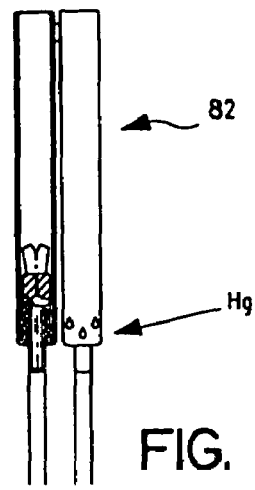
Figure 23C:
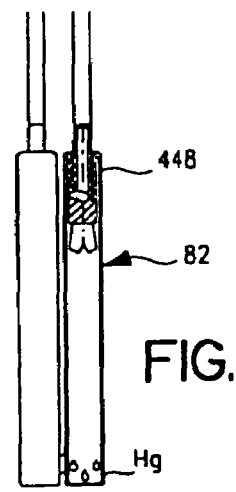
Figure 23D:
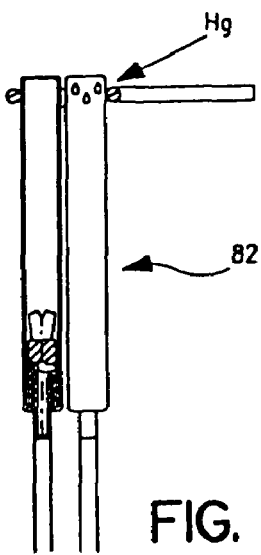

FIGS. 23B-D show a UV bulb assembly 82 operating under three experimental conditions. Output from these assemblies are shown FIG. 24 in the form of a graph. In the first case, FIG. 23B, UV bulb assembly 82 is placed in an upright position, however, without condensing 0-ring 84 being present. In the second case, FIG. 23C, UV bulb assembly 82 is placed upside down such that condensed Hg tends to gravitate to end of bulbs 440 distal to base 448. Again, no heat sink is present. Finally, in FIG. 23D, UV bulb assembly 82 is placed in an upright position with condensing O-ring 84 present and a brass bar used as a heat sink to dissipate heat. The light intensity outputs of these experimental UV lamp assemblies 84 were recorded at two separate times, $t_1$ and $t_2$. The outputs have been normalized against the highest output recorded at time $t_2$.

Figure 24:
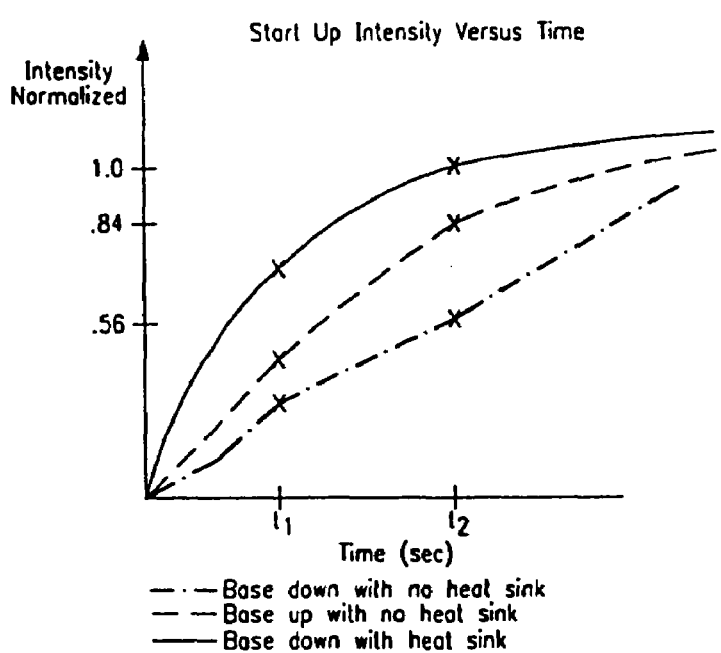
FIG. 24 is a graph of relative light intensity produced by the UV bulb assemblies of FIGS. 23B-D.

From the graph shown in FIG. 24, it is seen that the third case with UV bulb assembly 82 having its base down and using a heat sink, produces the highest normalized intensity of 1.0 at time $t_2$. The second best performance occurred in the second mbodiment with the base inverted or up and no heat sink used, resulting in a normalized output of 0.84 times that of the third case. Finally, the first case with no heat sink and with the UV bulb assembly in an upright position produced the slowest startup for the UV bulb assembly 84 with only 0.56 times the intensity of the base down/heat sink of the third case. Hence, the presence of condensing O-ring 84 is advantageous in the present invention where use of a UV bulb assembly 84 is desired which has virtually instantaneous startup and intensity. This rapid build up to maximum intensity allows lamp assembly 24 to be operated intermittently rather continuously while still providing satisfactory destruction of microorganisms. Although not used in the present embodiment, other additional heat sinks could be used such as an Al foil wrapped about O-ring 84.

Light pipe 252 will now be described in greater detail. Light pipe 252 is preferably made of acrylic, designated as V826, which is generally clear with a 1% let down or ratio of fluorescent green dye mixed in. The green dye is available from Uniform Color of Holland, Michigan under their designation 60-3170. This dye is adapted to fluoresce when stuck by the UV light, such as light 254 nm in wavelength, resulting in the emission of visible light in the green range. The green color has proven to provide a very efficient transfer of light through light pipe 252 while severely inhibiting the passage of other colors. For example, the blue light portion produced by the mercury in UV lamp assembly 72 does pass through light pipe 252 so that the light is visible from the outside of WTS unit 10 when UV light is not striking light pipe 252. Accordingly, a user can tell by the presence of a blue glow whether lamp assembly 24 is operating or not. However, the intensity of blue light allowed to pass through light pipe 252 is greatly diminished. Consequently, a light sensor on electronic assembly 66 primarily senses the intensity of visible light created by the fluorescing due to UV light striking pipe 252 and not other visible light produced by lamp assembly 24. Hence, light pipe 252 operates almost as a band pass filter.

Figure 25A:
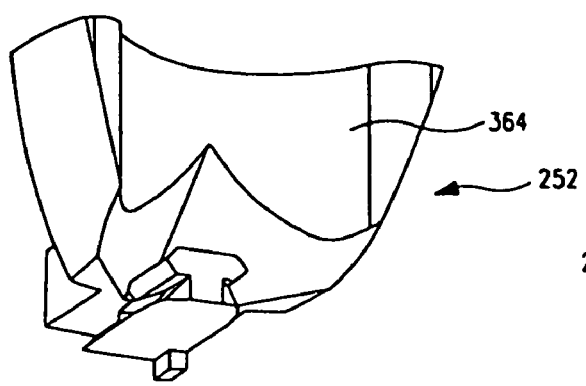
FIGS. 25A-F are enlarged front perspective, top, rear, front, bottom and side views of a light pipe.
Figure 25D:
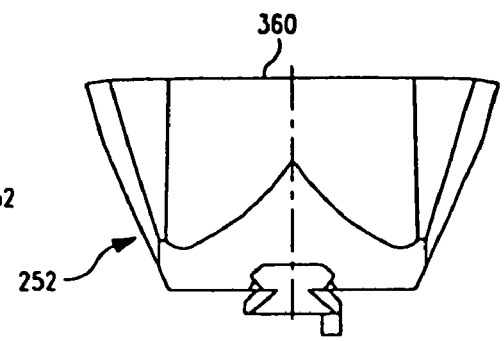
Figure 25B:
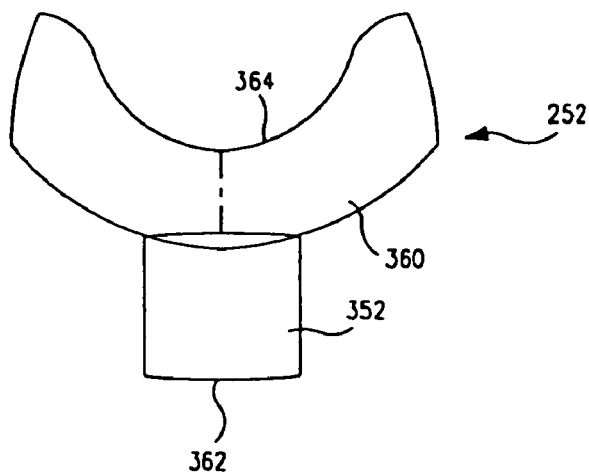
Figure 25E:
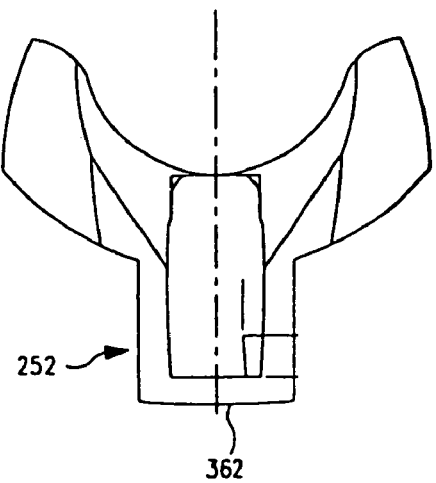
Figure 25C:
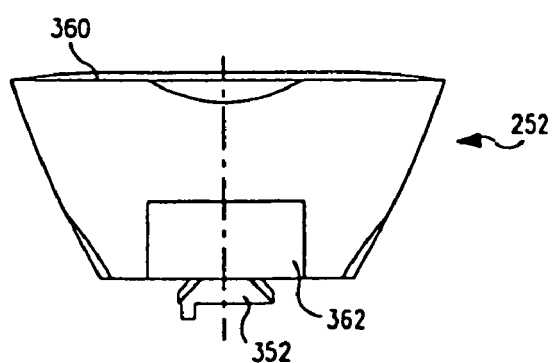
Figure 25F:
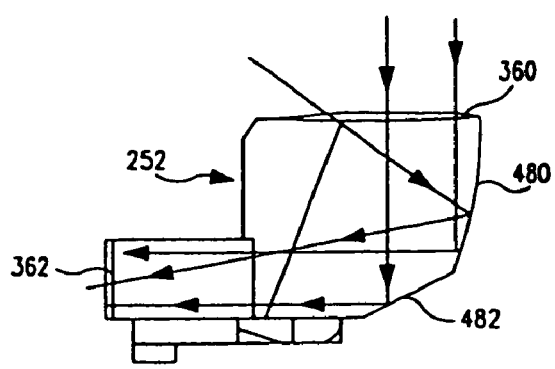
Figure 39:
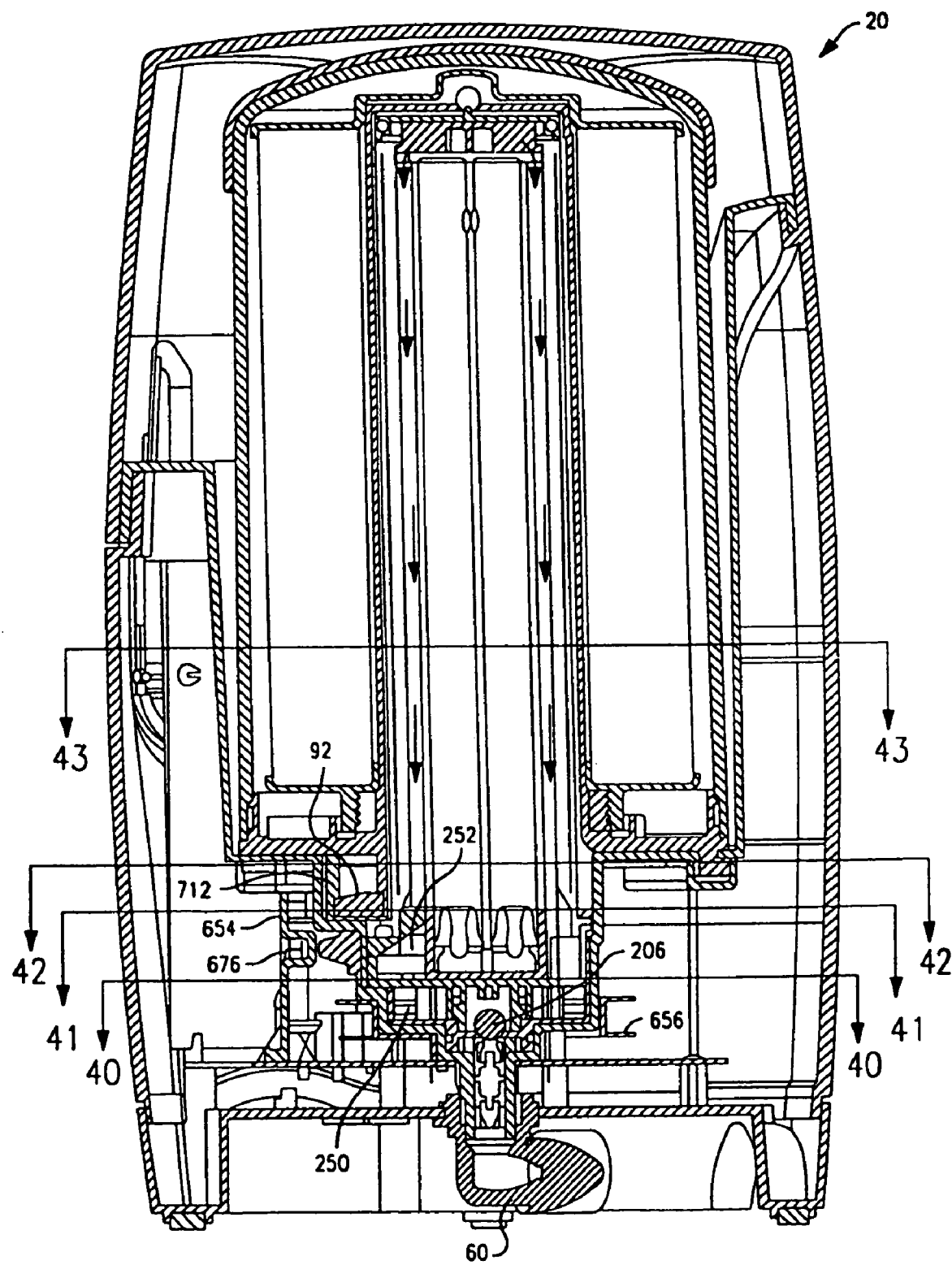
FIG. 39 is an enlarged sectional view taken along line 39-39 of FIG. 40.

Geometrically, light pipe 252 has a front curved inboard surface 364 and a top surface 360. Also, at the end of mounting block 352 is a light emitting outboard surface 362. Both top surface 360 and emitting outboard surface 362 are highly polished to readily receive or transmit light rays. Most of the light entering inboard surface 364 is from the filament ar a of UV bulb assembly 82 as light pipe 252 is disposed adjacent filaments 444 as best seen in FIG. 39. The light emitted from filaments 444 is generally in the red range of visible light and is not readily transmitted through light pipe 252. As shown in FIGS. 25C and 25F, top surface 360 is slightly curved and slants downwardly from inboard face 364 toward outboard surface 262. This allows top surface 360 to be focused toward the mid-length of mirrored reflectors 402 and also to receive UV light from the majority of lamp assembly 24. When UV light strikes top surface 360, the dye in light pipe 252 fluoresces and emits light in the green visible light spectrum. This visible green light is reflected by internal surfaces of light pipe 252 and directed out of emitting outboard surface 362, as suggested by FIG. 25F. By utilizing a green florescent dye in light pipe 252, it has been found that the intensity of visible light output from light pipe 252 is generally linearly proportionally to the UV light created within lamp assembly 24. Accordingly, by sensing visible light emitted from emitting outboard surface 362, the intensity of UV light in lamp assembly 24 can be directly monitored. If this output were not linear, a computer chip and look up table could be utilized to establish the relationship between the output of light from outboard surface 362 and UV light intensity output by bulb assembly 82. However, this additional need for a computer chip and look up table would greatly increase the complexity and cost of the monitoring circuitry. The measuring of visible light rather than UV light allows an inexpensive visible light detector and acrylic light pipe to be used rather than requiring the use of a more expensive UV light detector and quartz windows or light pipes.

The present invention also envisions the possibility of monitoring the color output from light pipe 252 to monitor the temperature of lamp assembly 24. When UV lamp assembly 82 is not outputting UV light, but instead, is just transmitting visible light produced by the filaments or the neon-argon gas mixture, light of very low intensity is output from outboard surface 362. Also, the color may differ from that of the green usually output when bulb assembly is operating at a high intensity.

Lamp assembly 24 is assembled as follow. The first step is to assemble bottom support assembly 76. As suggested in FIG. 10A, O-rings 244 are captured between base support 240 and bottom shield 242. Smart chip 250 is press fit into pocket 296 and light pipe 252 is dove-tailed mounted above pocket 296. Base support 240 and bottom shield 242 are then sonically welded together. Referring to FIG. 8A, secondary coil 74 is mounted by tangs 322 to bayonet openings 266 on base support 240 with leads 330 extending away from bottom support assembly 76. Top support assembly 78 is next assembled, as suggested in FIG. 16, with quartz O-rings 372 being captured between top cap 366 and top shield 368 which are sonically welded together. O-ring 370 is held within groove 382 in top cap 422.

UV bulb assembly 82 is placed in bulb receiving ribs 294 of bottom support assembly 76 with leads 440 extending through slots 270 and 272 of base support 240. Then, quartz sleeves 80 are pushed down into the O-rings 244 of base assembly 206. Next, condensing O-ring 84 is slid down over the top of UV bulb assembly 82 to maintain the correct positioning between quartz sleeves 80 and bulbs 440. Top support assembly 78 is then placed over quartz tubes 80 with quartz O-rings 372 sealing about the exterior of quartz tubes 80.

Reflectors 402 are juxtapositioned within respective enclosures 400 with glue being applied between curved portions 404 of enclosures 400 and curved portions 432 of enclosures 402. A first enclosure and reflector assembly 86 is laid down horizontally in a fixture (not shown). Then the assembly consisting of the UV bulb assembly 82, quartz tubes 80, bottom and top support assemblies 76 and 78 are placed in one half of assembly 86. Then the remaining half of the reflector and enclosure assembly 86 is brought down over the first assembly 86 with pilot pins 408 pressing into mating holes 410. The two enclosure assemblies 86 are sonically welded together with flanges 407 along each side of enclosures 400 being sonically welded together.

Next base assembly 72 is attached to bottom support assembly 76. Ball 206 is first inserted into pocket 222 of base 200. Base assembly 72 is then mounted beneath bottom support assembly 76 with light pipe 252 extending out pocket 226 of base assembly 72. Accordingly, when UV light from UV bulb assembly 82 strikes light pipe 252, visible green light is seen outside of lamp assembly 24. Manifold seal 204 effects a seal between base 200 and base support 240.

C. Base Unit

Figures 26A, 26B:
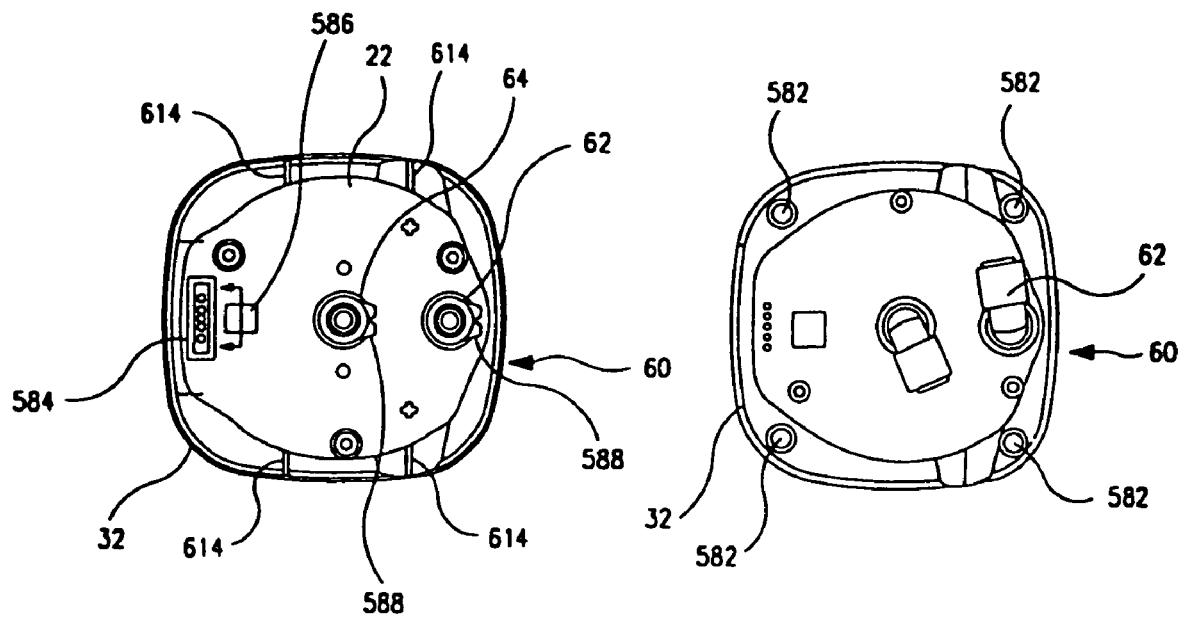
FIGS. 26A-C are a top plan view, a bottom plan view and an exploded perspective view of a bottom shroud assembly.
Figure 26C:
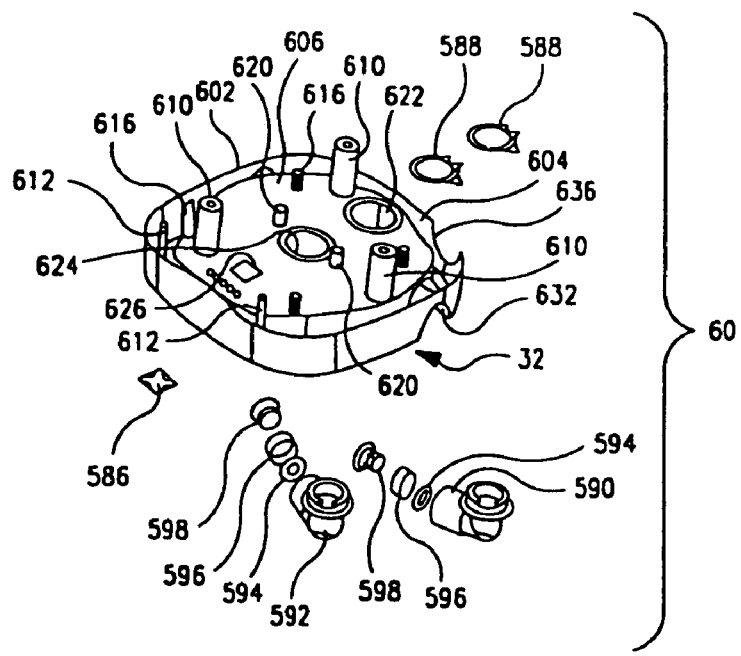
Figure 27A:
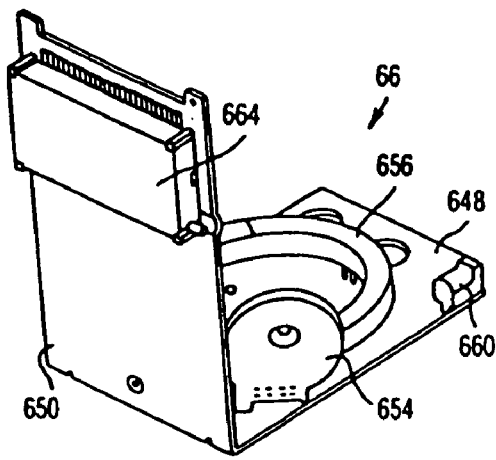
FIGS. 27A-F are a rear perspective view, a front elevational view, a rear elevational view, a top plan view, a side elevational view and a bottom plan view of an electronics assembly.
Figure 27D:
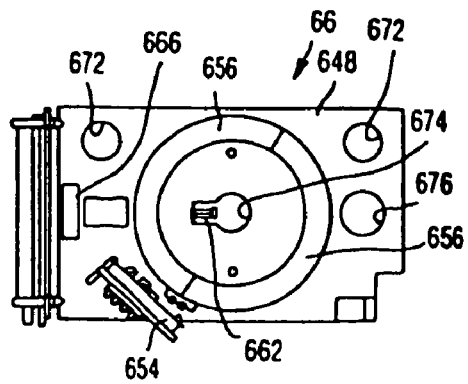
Figure 27B:
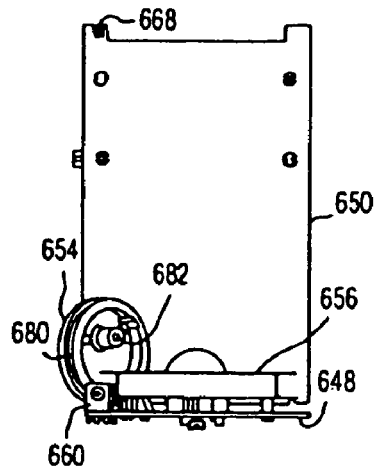
Figure 27E:
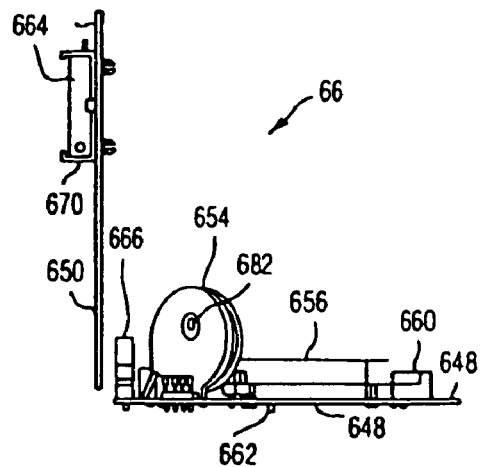
Figure 27C:
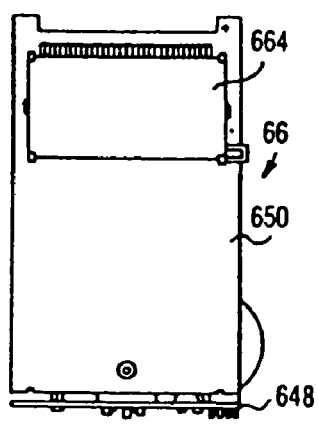
Figure 27F:
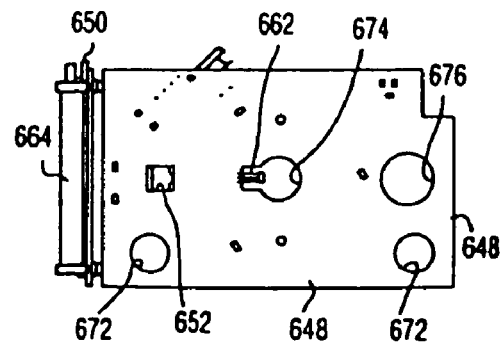

FIGS. 26A-C show a bottom shroud assembly 60 in top, bottom, and exploded views. Bottom shroud assembly 60 includes bottom shroud 32, inlet and outlet elbow assemblies 62 and 64, four foot pads 582, a speaker screen 584, a telephone jack cover 586 and a pair of C-clips 588. C-clips 588 secure inlet and outlet elbow assemblies 62 and 64 to bottom shroud 32. Inlet and outlet elbow assemblies 62 and 64 are comprised of inlet elbow 590, outlet elbow 592, O-rings 594, collets 596 and adapter 598.

Bottom shroud 32 is shown in FIG. 26C. An outer perimeter wall 602 is disposed adjacent a recess 604 which surrounds a raised platform 606. Three threaded bosses 610 are adapted to receive screws which secure inner sleeve 50 to bottom shroud 32. A pair of raised ribs 61.2 and four retaining ribs 614, which extend between perimeter wall 602 and raised platform 606, are used to position back and front shrouds 34 and 36. Similarly, four raised cross-shaped ribs 616 are used to support electrical assembly 66. Two positioning bosses 620 are used to pilot mounting pins on outlet cup 58. Inlet and outlet openings 622 and 624 are sized to received elbows 62 and 64 using C-clips. Square opening 626 is adapted to provide access to a phone jack on electrical assembly 66. Arches 632 and 634 are formed on the underside of bottom shroud 22 to accommodate inlet and outlet hoses (not shown) delivering water to and from WTS unit 20.

Electronics assembly 66 is displayed in FIGS. 27A-F. Components of electronics assembly 66 include a lower board 648, an upper board 650, a phone jack 652, a primary coil 656, a smart sensor assembly 654, a power jack 660, a flow hall effect sensor 662, a VFD 664, a speaker 666 and a magnet sensor 668. Primary coil 656 holds 10 turns of wire. A clip 670 holds VFD 664 to upper board 650. Lower board 648 has a pair of support access boss openings 672, an outlet opening 674 in which sensor 662 is disposed, and an inlet opening 676. Support access openings 672 allow passage of bosses 610 on bottom shroud 32. Inlet and outlet openings 674 and 676 accommodate water passages entering and exiting relative to inner sleeve 50 and outlet cup assembly 56. The perimeter of lower board 648 is configured to be supported by stepped ribs 616 of bottom shroud 22. Smart sensor assembly 654 includes a coil 674 and a light sensor 676. Coil 674 is arranged to transpond with and power filter and lamp assembly smart chips 112 and 250. Light sensor 676 receives visible light output from light pipe 252. Magnet sensor 668 is mounted on upper board 650 to sense when top shroud 40 and magnet 70 are properly mounted over the remainder of base unit 22.

Figure 28A:
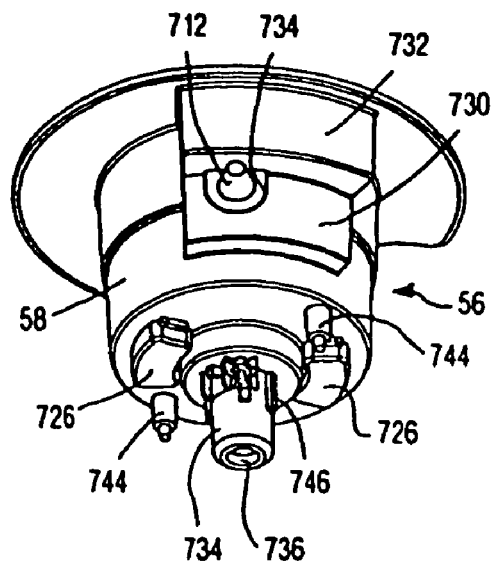
FIGS. 28A-D are a bottom perspective view, a top plan view, a sectional view taken along line 28C-28C of FIG. 28B and a sectional view taken along line 28D-28D of FIG. 28B of an outlet cup assembly.
Figure 28B:
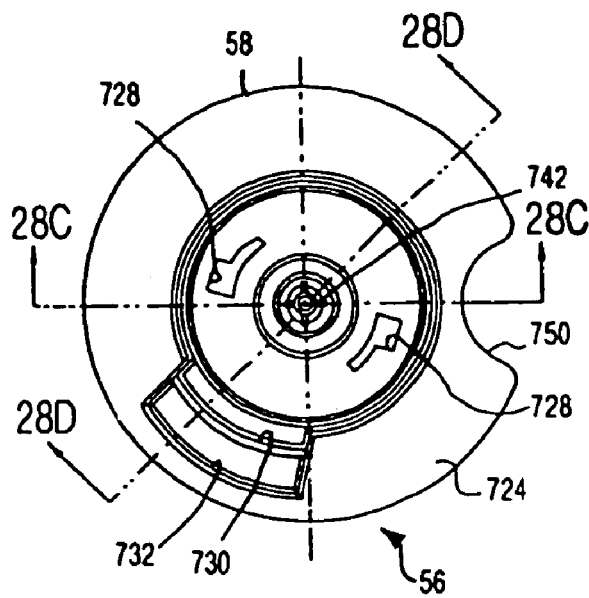
Figure 28C:
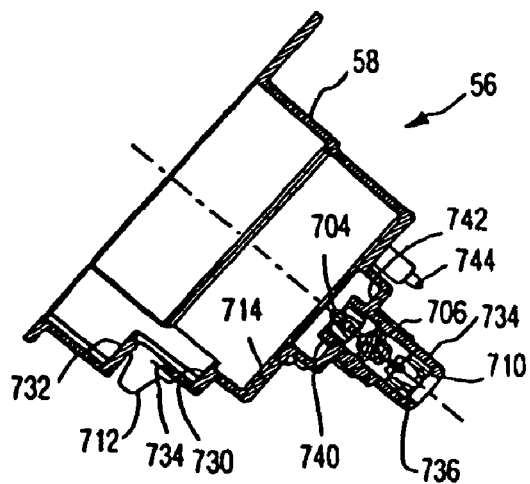
Figure 28D:
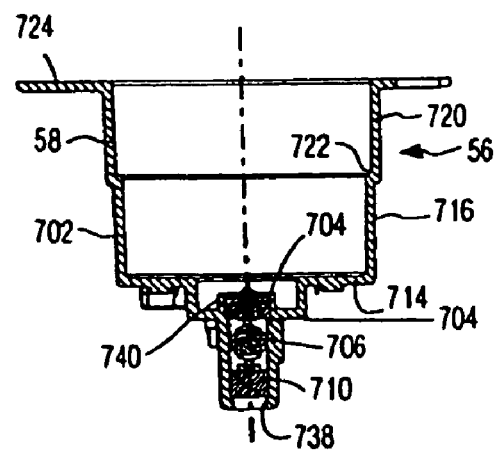

Outlet cup assembly 56, as illustrated in FIGS. 28A-D, includes outlet cup 58, an upper bearing 704, a flow regulator 706, a lower bearing 710, and a light pipe cup 712. Outlet cup 58 has a base wall 714, lower and upper side walls 716 and 720 joined by a step 722 and an upper flange 724. Referring to FIG. 28B. a pair of retaining covers 726 are sonically welded to base wall 714 to seal about L-shaped openings 728 formed in base wall 714. Openings 728 serve to bayonet mount tangs 232 located on the bottom of lamp assembly 24. Formed in portions of lower and upper side walls 716 and 720 are lower and upper steps 730 and 732. Steps 730 and 732 accommodate the rotation of light pipe 252 and pocket 296 as lamp assembly 24 is twisted to mount and dismount relative to outlet cup assembly 56. An opening 734 in lower wall 716 allows light pipe cup 712 to be mounted therein. When lamp assembly 24 is locked in place in outlet cup assembly 56, light pipe 252 is aligned with opening 734 and light pipe cup 712. Light pipe cup 712 is aligned with light sensor 676, as is displayed in FIG. 41.

Downwardly depending from base wall 714 is a conduit 736 with a passageway 738 extending therethrough. A collar 740 is formed on the upper end of conduit 736. The inside of passageway 738 has four longitudinally extending slots 742. Each of upper and lower bearings 704 and 710 has ribs (not shown) thereon which are received in slots 742 to prevent rotation of bearings 704 and 710 relative to outlet cup 58. Note that upper bearing 704 has a pointed upper end and extends above collar 740. When lamp assembly 24 is mounted to outlet cup 58, upper bearing 704 will unseat check ball 206 held in base 200 of lamp assembly 24 allowing water to pass to flow regulator 706 and then to outlet elbow assembly 64. When lamp assembly 24 is removed from outlet cup 58, check ball 206 will reseat and prevent water from spilling from the bottom of lamp assembly 24.

Lower and upper bearings 704 and 710 rotatably support flow regulator 706 which has a pair of spiral blades thereon. Imbedded in one of the blades is a magnetic chip. As flow regulator 706 spins, flow hall effect sensor 662 picks the passing magnetic field created by the magnetic chip thereby sensing the flow rate of the WTS unit 20. Located on the bottom side of base wall 714 is a pair of stepped positioning pins 744 which are configured to be received in bosses 620 of bottom shroud 32. A cutout 750 is formed in flange 724 to accommodate a water carrying conduit on inner sleeve 50.

Figure 29C:
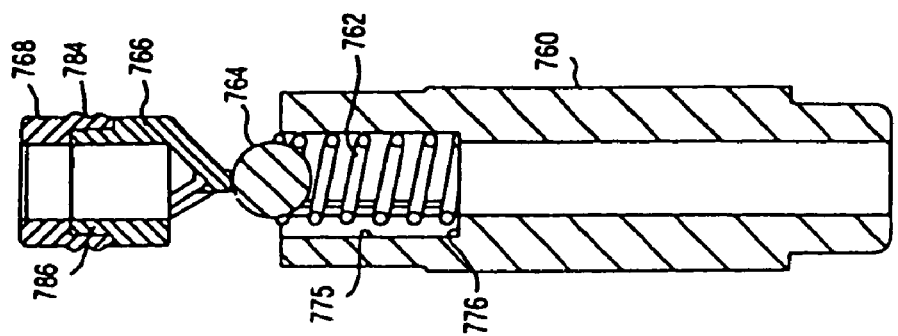
FIGS. 29A-C are an exploded view, an elevational view and a sectional view taken along line 29C-29C of FIG. 29B of an inlet valve assembly.
Figure 29B:
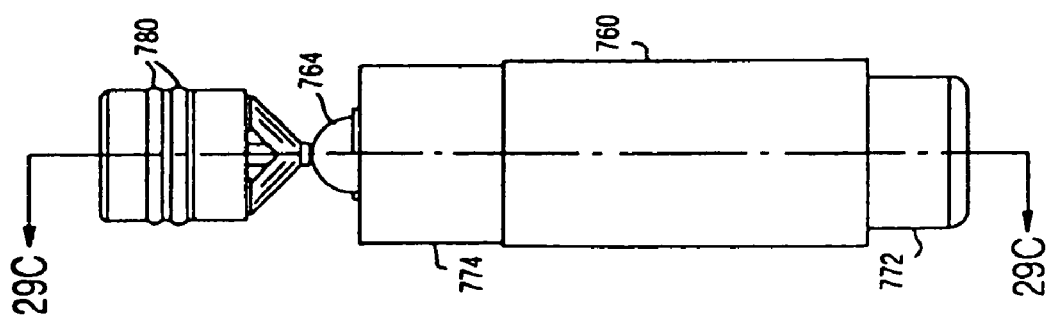
Figure 29A:
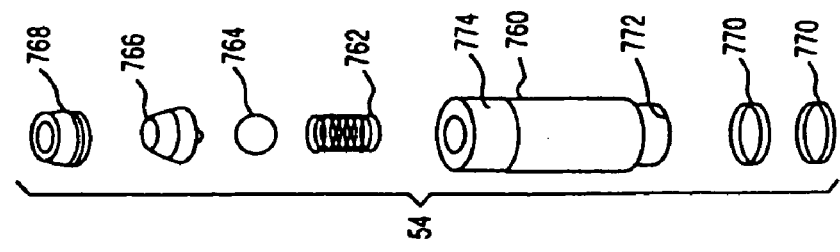

As best seen in FIG. 37, inlet valve assembly 54 mounts in inner sleeve 50 and fluidly connects inlet elbow assembly 62 of lower shroud assembly 60 with inlet opening 172 of filter assembly 26. FIGS. 29A-C individually illustrate inlet valve assembly 54. Components of inlet valve assembly 54 include inlet valve housing 760, inlet spring 762, inlet check ball 764, inlet offset 766, inlet cup seal 768 and a pair of elastomeric O-rings 770. Inlet valve housing 760 has a pair of reduced diameter end portions 772 and 774 for receiving O-rings 770. An inner bore 775 in inlet valve housing 760 is stepped to include a seat 776 for receiving the end of inlet spring 762. Inlet check ball 764 rests upon inlet spring 762 and is depressible by inlet offset 766 when filter assembly 26 is mounted in inner sleeve 50. When a filter assembly 26 is removed from WTS unit 20, inlet check ball 764 seats preventing water from passing through inlet valve assembly 54 and to the chamber vacated by the absent filter assembly 26. A pair of sealing beads 780 are formed on the outside of inlet cup seal 768 which assist in sealing with inner sleeve 50. Inlet offset 766 and inlet cup seal 768 have interlocking ribs and grooves 784 and 786 to prevent relative rotation therebetween.

Figure 30A:
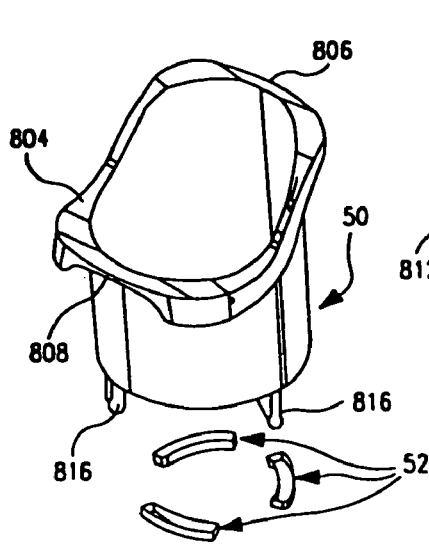
FIGS. 30A-C are an exploded perspective view, a top plan view and a bottom plan view of an inner sleeve assembly.
Figure 30B:
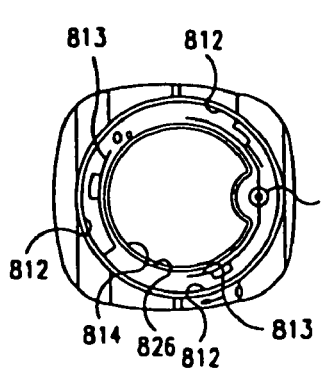
Figure 30C:
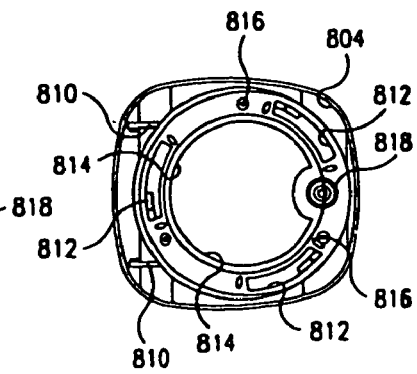

FIGS. 30A-C show inner sleeve 50 and three covers 52. FIGS. 31A-D shows inner sleeve 50 with outlet cup assembly 56 welded thereto. Inner sleeve 50 has a circumferentially extending flange 804 extending about its upper perimeter. Inner sleeve 50 has a raised back portion 806 which curves downwardly to meet a lower front portion 808. Formed in the front of front portion 808 are a pair of spaced apart slotted retaining ribs 810 for retaining upper circuit board 650. Looking to FIGS. 30B and C, the base of inner sleeve 50 includes three L-shaped retaining openings 812 for receiving retaining tangs 180 on filter assembly 26. Adjacent openings 812 are three ramps 813 which cooperate with corresponding ramped scallops 178 on the bottom of filter assembly 26. Ramps 812 and scallops 178 help lower and raise filter assembly 26 when filter assembly 26 is installed or removed from inner sleeve 50. Covers 52 are welded beneath respective retaining openings 812 to seal the bottom of inner sleeve 50 against leakage. A central opening 814 is formed in the bottom of inner sleeve 56 to receive outlet cup assembly 56. Three spacer legs 816 are circumferentially spaced about the base of inner sleeve 50 and are designed to cooperate with the three bosses 610 to receive screws which affix bottom shroud 22 to inner sleeve 50. Screws pass through bosses 610 and tap into holes 817 in spacer legs 816.

Figure 31A:
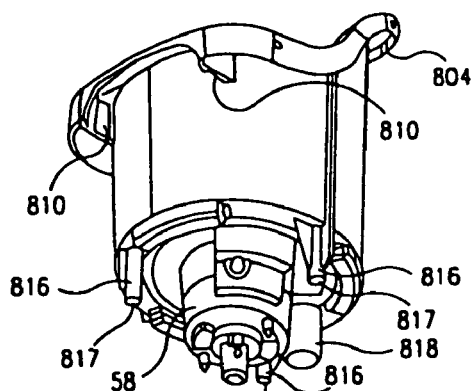
FIGS. 31A-D are a perspective view, a bottom plan view, a front elevational view and a sectional view taken along line 31D-31D of FIG. 31B of an inner sleeve and outlet cup assembly.
Figure 31B:
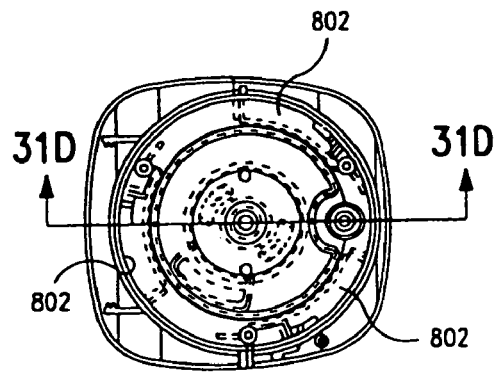
Figure 31D:
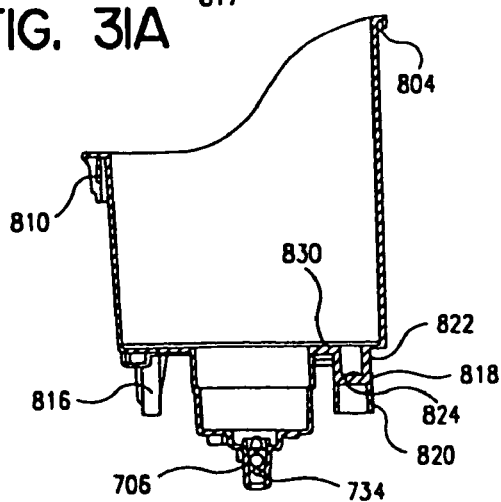
Figure 31C:
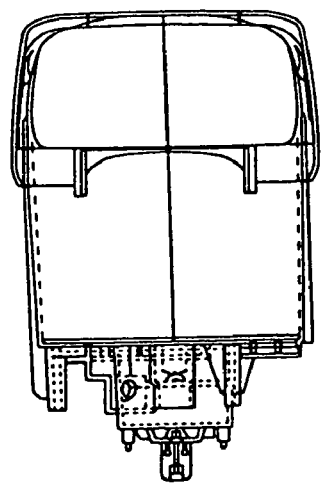
Figure 32A:
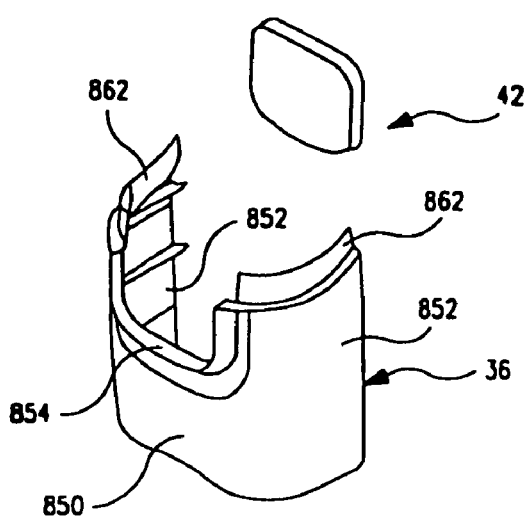
FIGS. 32A-C are an exploded perspective view, a top plan view and a front elevational view of a front shroud and lens assembly.
Figure 32B:
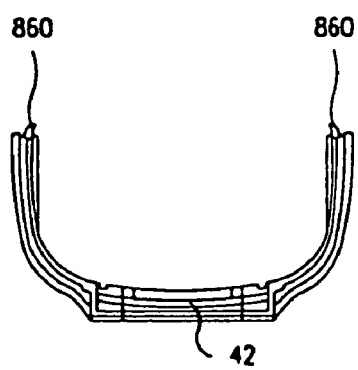
Figure 32C:
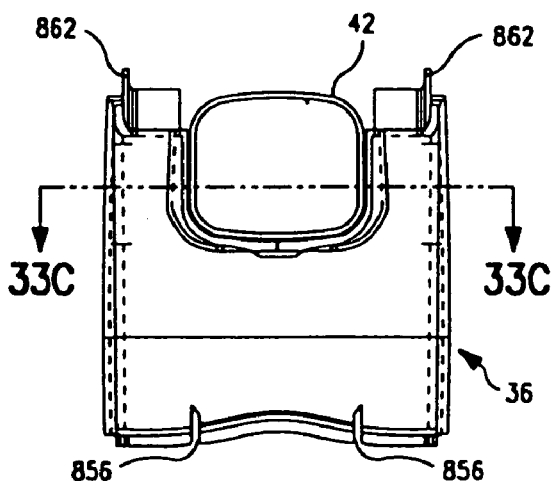

A water inlet conduit 818 is formed in the base of inner sleeve 50. As best seen in FIGS. 31D and 37, conduit 818 includes a lower conduit portion 820, an upper conduit portion 822 and an intermediate neck portion 824. Lower conduit portion 820 receives spring 762 and ball 764 of inlet valve assembly 54 while upper conduit portion 822 slidably retains inlet offset 766 and inlet cup seal 768. Surrounding central opening 814 is a step 726. Step 726 mates with flange 724 on outlet cup assembly 56 so that a sonically welded joint 730 can be formed therebetween.

Figure 33A:
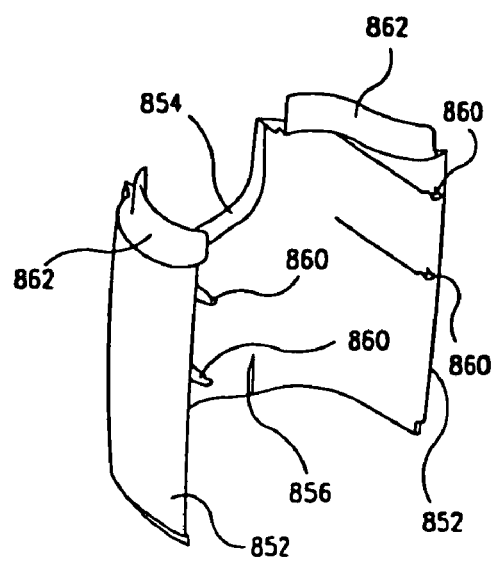
FIGS. 33A-C are a rear perspective view, a rear elevational view, and a top plan view of the front shroud.
Figure 33B:
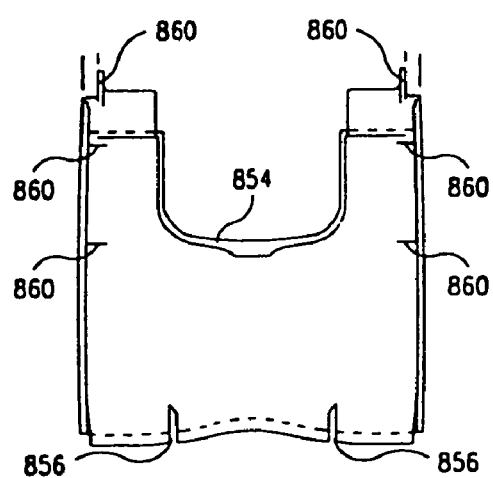
Figure 33C:
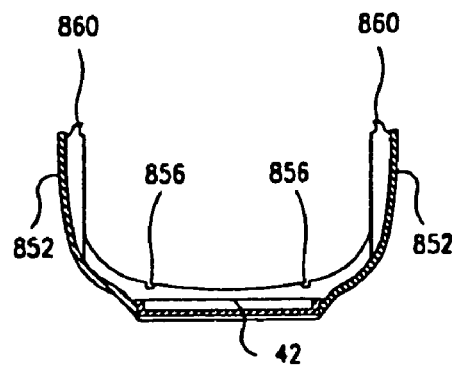
Figure 34A:
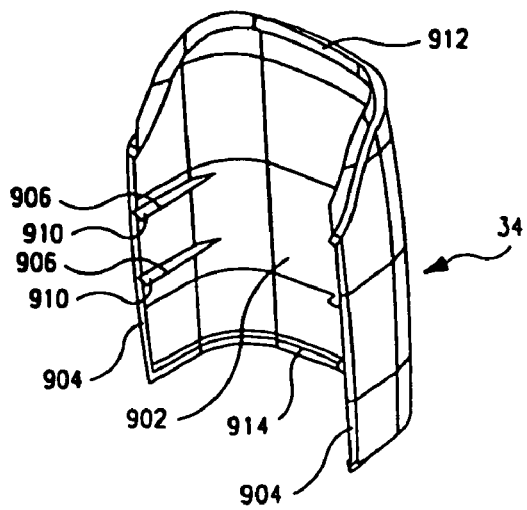
FIGS. 34A-E are a front perspective view, a rear perspective view, a top plan view, a rear elevational view and a side elevational view of a back shroud.
Figure 34B:
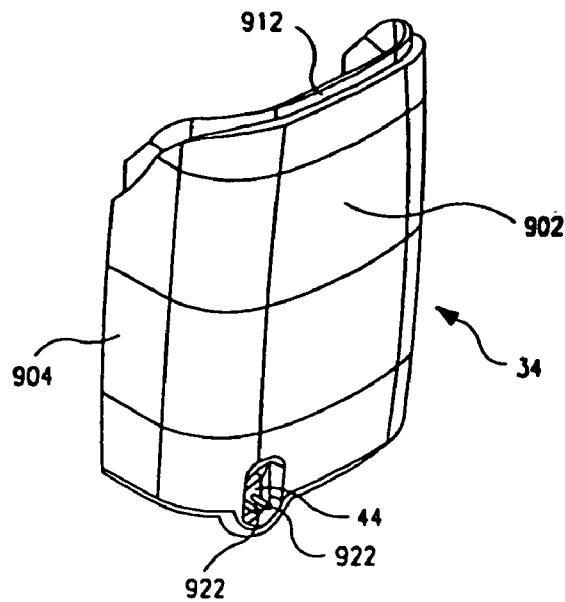
Figure 34C:
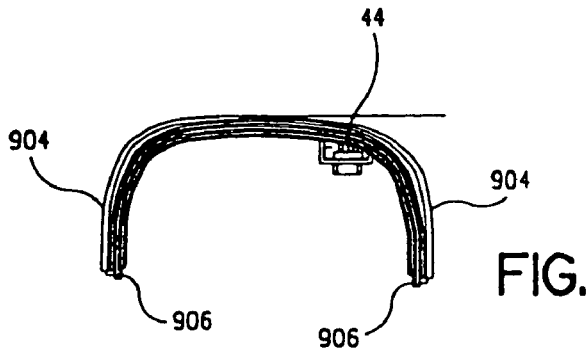
Figure 34D:
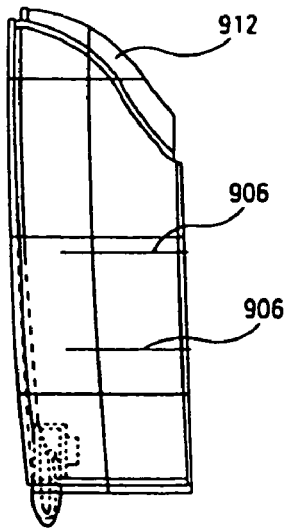
Figure 34E:
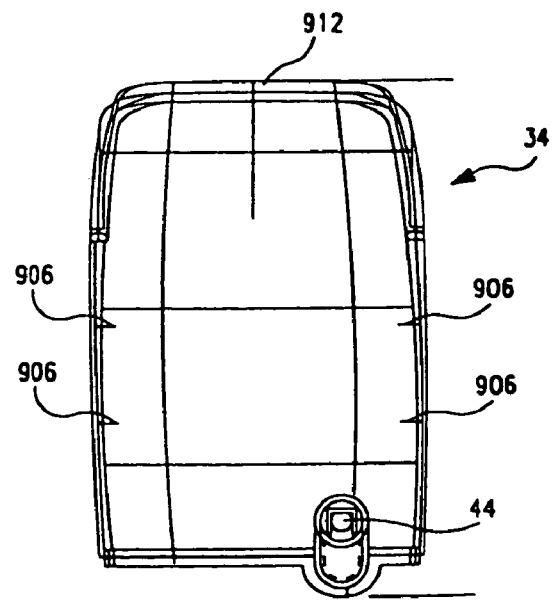

Turning now to FIGS. 32A-C and FIGS. 33A-C, lens 42 and front shroud 36 are displayed. Front shroud 36 is generally U-shaped having a front portion 850 and a pair of side portions 852 extending rearwardly. Formed in the front of front portion 850 is lens receiving opening 854 adapted to receive the lower edge and sides of lens 42. A pair of vertical slots 856 are located in the bottom of front portion 850. Two pairs of hooked projections 860 extend rearwardly along the insides of side walls 852. Located atop side walls 852 are respective contoured flanges 862. As best seen in FIG. 33C, lens 42 interlocks with lens receiving opening 854. Prior to assembly with other components, lens 42 is sonically welded to lens receiving opening 854 to form an assembly.

Back shroud 34 is illustrated in FIGS. 35A-E. Back shroud 34 includes a back portion 902 and a pair of forwardly extending side portions 904. Extending forwardly along the inside of side portions 904 are two pairs of inner ribs 906. At the forward end of each of ribs 906 is a retaining recess 910 which is configured to releasably cooperate with hooked projections 860 of front shroud 36. A contoured and stepped top flange extends across the top of back shroud 34. Similarly, a bottom flange 914 runs across the bottom of back shroud 24 and is shaped to be received within recesses in bottom shroud 34. Power plug assembly 44 extends through and is retained by the lower portion of back portion 902.

FIGS. 35A and B shows top shroud 40, magnet holder 68 and magnet 70. FIGS. 36A-D shows top shroud 40 independently. Top shroud 40 includes a front portion 940, a pair of side portions 942, a rear portion 944 and a top wall 946. A lower flange 948 extends about the lower periphery of top shroud 30 and is configured to match with the upper flanges of back and front shrouds 24 and 26. An upper lens receiving opening 950 is formed to match the contours of the upper portion of lens 932. Magnet holder 68 is mounted adjacent opening 950 and holds magnet 70 in the proximity of a magnet sensor 668 on electrical assembly 66. This magnet 70 and sensor 668 operate to cut off power to WTS unit 20 power when top shroud 40 is removed.

D. Assembly and Operation

Base unit 22 is assembled as follows. Inner sleeve 50 is placed upside upon a fixture (not shown.) Covers 52 are sonically welded to the bottom of inner sleeve 50 to form an inner sleeve assembly. Outlet cup assembly 56 is next assembled. Outlet cup 58 has covers 726 sonically welded thereto. Upper and lower bearings 704 and 706 and flow regulator 706 are positioned within passageway 736 in the bottom of outlet cup 58. Also, light pipe cup 712 is installed in opening 734 of outlet cup 58. Outlet cup assembly 56 is then placed within the bottom of inner sleeve 50 with flanges 724 being welded to inner sleeve 50 adjacent central opening 814 to form weld joint 830. Next inlet valve assembly 54 is installed in conduit 818 of inner sleeve 50 as suggested in FIGS. 29A-C and 37. Inlet valve housing 760, inlet spring 762 and inlet check ball 764 are placed within lower conduit portion 820 of conduit 818 with O-ring 770 creating a seal between the upper portion of inlet valve housing 760 and lower conduit portion 820. Inlet cup seal 768 and inlet offset 766 are placed within neck portion 824 of conduit 818 with seal rings 780 sealing within conduit 818.

Electronics assembly 66 is next attached to the inner sleeve assembly. Lower board 748 is placed over the bottom of outlet cup 58. Flanges on upper board 650 are received within slotted retaining ribs 810 in the front of inner sleeve 50. Lens 42 is sonically welded to front shroud 36. Front shroud 36 and back shroud 34 are then attached to inner sleeve 50. VFD display 664 on electronics assembly 66 is aligned with lens 42.

Figure 40:
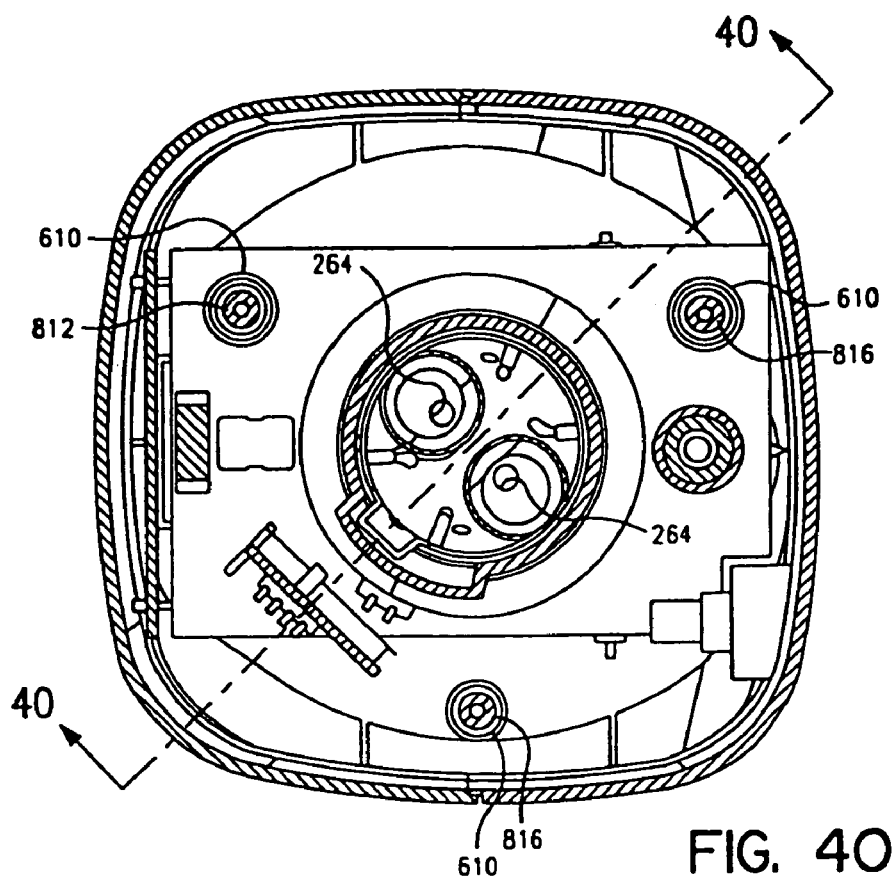
FIG. 40 is a sectional view taken along line 40-40 of FIG. 39.
Figure 41:
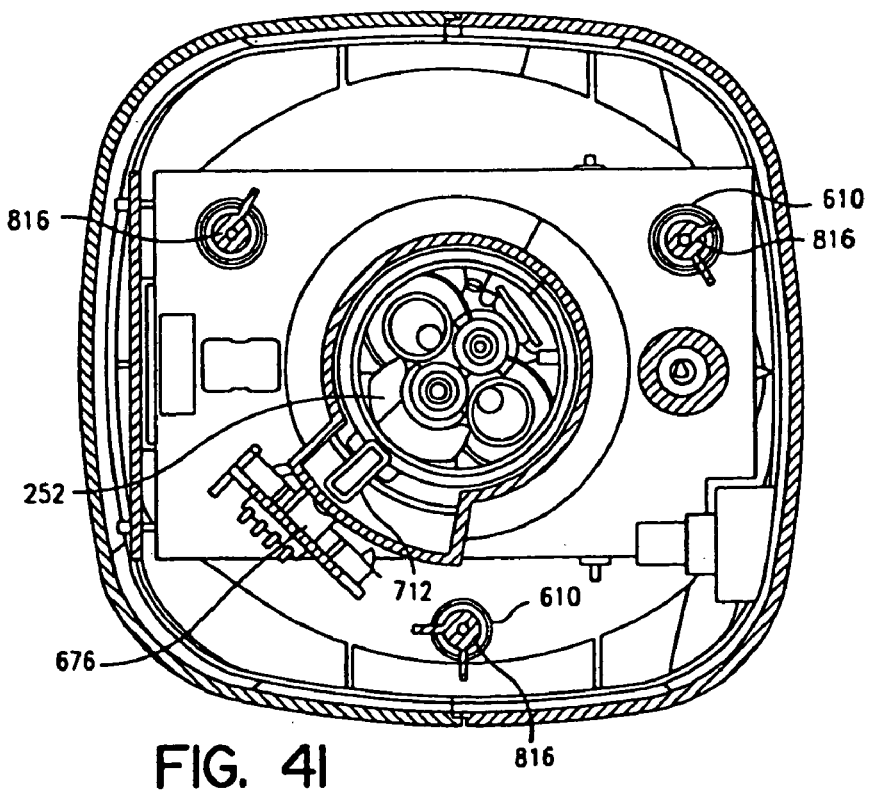
FIG. 41 is a sectional view taken along line 41-41 of FIG. 39.
Figure 42:
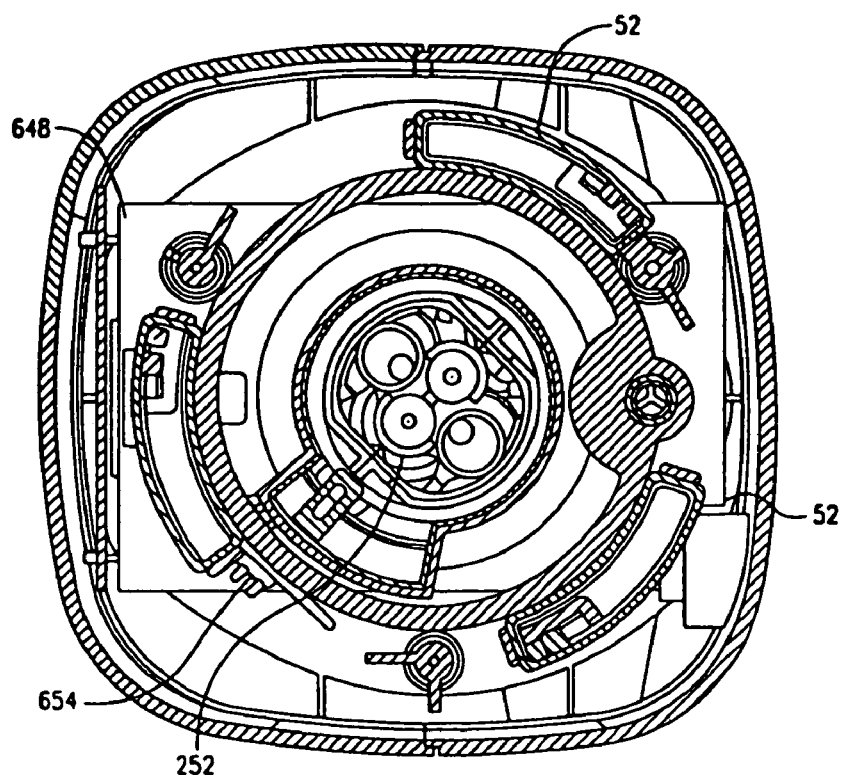
FIG. 42 is a sectional view taken along line 42-42 of FIG. 39.
Figure 43:
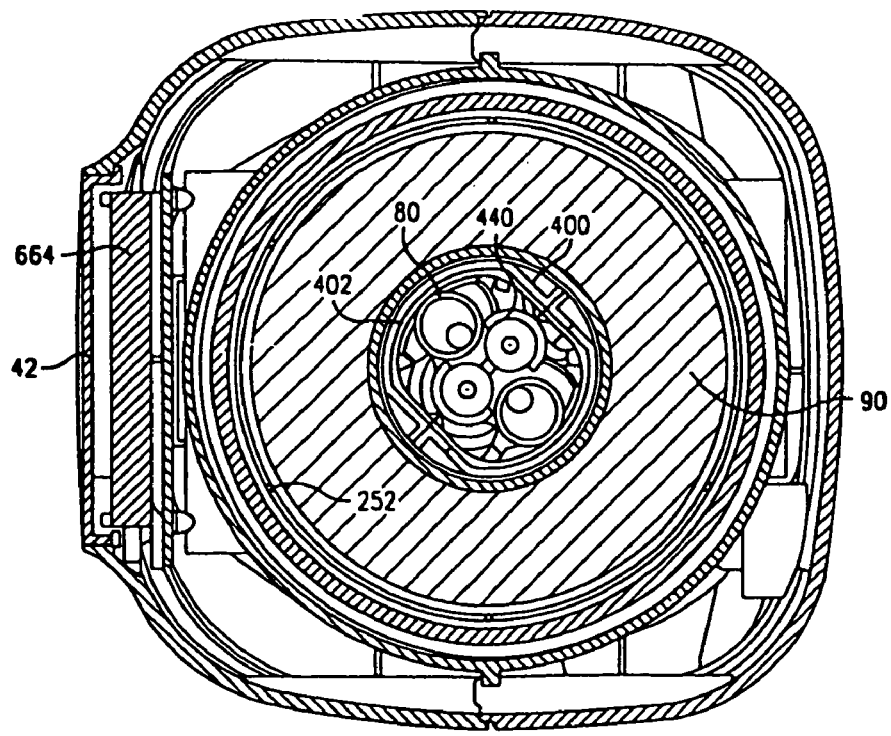
FIG. 43 is a sectional view taken along line 43-43 of FIG. 39.

Bottom shroud assembly 60 is next assembled. Inlet and outlet elbow assemblies 62 and 64 are secured to bottom shroud 32. Bottom shroud assembly 60 is placed over electronics assembly 66 and outlet cup assembly 58. Raised ribs 612 provide support to the edges of lower board 748. Inlet and outlet elbow assemblies 62 and 64 respectively receive lower step 772 of inlet valve housing 760 and conduit 736 of outlet cup 58. Stepped positioning pins 744 pass through lower board 748 and are received in positioning bosses 620 of bottom shroud 32. Two of mounting bosses 610 pass through boss openings 672 in lower board 748. The third boss 610 passes outside of lower board 748 as can be seen in FIGS. 40 and 41. Mounting bosses 610 match up with mounting legs 816 on inner sleeve 850. Three screws are inserted into mounting bosses 610 with screws self-tapping into openings 817 in mounting legs 816 securing bottom shroud assembly 60 to inner sleeve assembly and back and front shrouds 34 and 36 completing the assembly of base unit 22, with the exception of top shroud 40.

Lamp assembly 24 is bayonet mounted with retaining tangs 232 releasably engaging with L-shaped retaining openings 726 of outlet cup 58. In a similar manner, filter assembly 26 is coaxially placed over lamp assembly 24 with retaining tangs 180 of filter assembly 26 bayonet mounting to L-shaped retainer openings 812 on inner sleeve 50. As filter assembly 26 is mounted, filter assembly 26 lowers upon ramped recesses Top shroud 40 has magnet holder 68 attached thereto. Magnet 70 is then placed within magnet holder 68. Top shroud 40 is placed over filter assembly 26 and upon back and front shrouds 34 and 36 to complete assembly of WTS unit 20. Magnet 70 is located in the proximity of the magnet sensor of electronics assembly 66 thereby allowing WTS unit 20 to energize.

Looking to FIG. 37, water enters outlet assembly 62 beneath bottom shroud 32 and passes to inlet valve assembly 54. Inlet valve assembly 54 delivers water through inner sleeve 50 to reach inlet opening 172 of filter assembly 26 with the untreated water lifting inlet ball 100 from its seat 174. The untreated water passes beneath bottom filter end cap 106 and radially outwardly until striking filter housing 96. The untreated water then passes upwardly into the spaced formed between filter housing 96 and the radial exterior of filter block 90. The untreated water then filters radially inwardly passing through filter block 90 until reaching base and inner sleeve 92. Water passes upwardly until reaching top filter end cap 108. The now filtered water travels radially inwardly beneath cap portion 136 of filter end cap 108 and over top portion 154 of base and inner sleeve 92.

With lamp assembly 24 installed within filter assembly 26, button 376 atop lamp assembly 24 displaces outlet check ball 102 from its seat 164 on base and inner sleeve 92. The filtered water passes out of filter assembly 26 through its outlet opening 160 and enters lamp assembly 24 through opening 388 in top support assembly 78 and into quartz sleeves 80. The filtered water is irradiated with UV light from UV bulb assembly 82. UV bulb assembly 82 is powered by secondary coil 74 which receives power from primary coil 656 of electronics assembly 66. UV light produced within lamp assembly 24 strikes light pipe 252 causing the fluorescent dye therein to fluoresce and produce visible light. The visible light passes from light pipe 252 and through light pipe cup 712 to reach visible light sensor 676. Note that filter and lamp smart chips 112 and 250 are located in close proximity with smart sensor assembly 654.

Looking now to FIG. 38, the filtered water is irradiated with UV light from UV bulb assembly 82 until reaching bottom support assembly 76. Reflected UV light from reflectors 402 assist in increase the amount of light which is directed upon quartz sleeves 80. The filtered and irradiated water pass through openings 264 in bottom support assembly 76 and is collected in base 72. Water exits lamp assembly 72 through outlet opening 228 in base 72 as check ball 206 remains unseated by top bearing 704. The now fully treated water passes by and rotates rotor or flow regulator 706. Hall effect sensor 662 picks up the passing magnetic field created by spinning flow regulator 706 to determine the flow rate through WTS unit 20. The treated water then exits WTS unit 20 through outlet elbow assembly 60.

While in the foregoing specification this invention has been described in relation to certain preferred embodiments thereof, and many details have been set forth for the purpose of illustration, it will be apparent to those skilled in the art that the invention is susceptible to alteration and that certain details described herein can vary considerably without departing from the basic principles of the invention.

For example, rather than using a secondary water treatment device such as a lamp assembly which emits UV radiation needed to kill microorganisms, other treatment device may used. Examples may include an ozone generator, a dispenser of mineral additives, an ion exchanger or a device employing hollow fiber media for treating water. These secondary water treatment devices ideally would also be disposed in the chamber defined by the inner sleeve of a filter assembly. These secondary water treatment device may also be inductively powered by a primary coil in a base unit which controls the operation of the water treatment system. Also, a set of valves and seals may be employed to seal the secondary water treatment device in manner similar to that described above with respect to the base unit, filter assembly and and lamp assembly.

What is claimed:

1. A lamp assembly for use in a water treatment system comprising:
    a housing having an inlet opening and an outlet opening;
    a bulb assembly disposed within the housing to produce radiation, the bulb assembly including a bulb having a bulb longitudinal axis;
    at least one conduit connecting the inlet opening and the outlet opening transporting fluid through the housing, the conduit including a conduit longitudinal axis that is substantially parallel to the bulb longitudinal axis; and
    a reflector assembly disposed within the housing, said reflector assembly including at least two diminishing radii of curvature that terminate at a terminal curvature peak which projects toward and immediately adjacent the bulb, wherein substantially all light emitted from the bulb assembly is reflected away from the bulb assembly toward the at least one conduit to treat water flowing therethrough, wherein each of the diminishing radii of curvature transition at locations opposite the terminal curvature peak to corresponding constant radii portions of the reflector assembly, wherein the conduit is positioned adjacent at least one of the constant radii portions.

2. The lamp assembly of claim 1 wherein:
    the reflector assembly includes a second terminal curvature peak, and wherein the at least one conduit is positioned midway between the terminal curvature peaks of the reflector assembly so that the conduit receives light reflected from opposite sides of the reflector assembly.

3. The lamp assembly of claim 2 wherein:
    each of the pair of the reflectors are elongate and are omega shaped in cross-section, each of the pair of the reflectors having opposing generally curved central portions and a pair of opposing flanges which mate with one another.

4. The lamp assembly of 1 wherein:
    the reflector assembly includes at least one reflector having a planar portion joined with the terminal curvature peak, the planar portion extending outwardly away from the bulb assembly.

5. The lamp assembly of claim 1 further comprising:
    a lower end cap disposed at a lower portion of the lamp assembly.

6. The lamp assembly of claim 5 wherein:
the lower end cap is generally cup-shaped and includes a self-sealing valve to prevent liquid from escaping from the lower end cap.

7. The lamp assembly of claim 6 wherein:
the valve includes a check ball valve.

8. The lamp assembly of claim 1 further comprising:
a top end cap which includes the inlet.

9. The lamp assembly of claim 8 wherein:
the top end cap includes a button extending away from the bulb assembly.

10. The lamp assembly of claim 1 wherein:
a pair of elongate and curved enclosures wrap around the reflector assembly.

11. A lamp assembly for use in a water treatment system comprising:
a housing;
a conduit disposed within said housing and including a conduit longitudinal axis;
a bulb disposed within the housing to produce radiation, the bulb including a longitudinal axis that is substantially parallel to the conduit longitudinal axis; and
a reflector assembly including a plurality of diminishing radii of curvature that terminate at a terminal curvature peak which projects inwardly toward the bulb, the terminal curvature peak being positioned immediately adjacent the bulb, the reflector assembly reflecting substantially all radiation emitted from the bulb toward the conduit to treat water flowing therethrough, wherein at least one of the plurality of diminishing radii of curvature transition at an inflection point to corresponding constant radii portions, at least one of the constant radii portions being adjacent the conduit.

12. The lamp assembly of claim 11 wherein a first set of diminishing radii of curvature from the plurality of diminishing radii of curvature is positioned on a first side of the reflector assembly and a second set of the diminishing radii of curvature from the plurality of diminishing radii curvature is positioned on a second side of the reflector assembly, wherein the conduit is positioned midway between the first set of diminishing radii of curvature and the second set of diminishing radii of curvature so that the conduit receives radiation from the first set and the second set of diminishing radii of curvature.

13. The lamp assembly of claim 11 comprising a planar portion joined with the terminal curvature peak, the planar portion projecting outwardly and away from the bulb.

* * * * *